(12) United States Patent
Fischer et al.

(10) Patent No.: US 8,298,581 B2
(45) Date of Patent: Oct. 30, 2012

(54) MATRIX COMPOSITIONS FOR CONTROLLED DELIVERY OF DRUG SUBSTANCES

(75) Inventors: Gina Fischer, Væ rløse (DK); Daniel Bar-Shalom, Kokkedal (DK); Lillian Slot, Virum (DK); Anne-Marie Lademann, Charlottenlund (DK)

(73) Assignee: Egalet A/S, London (GB)

( * ) Notice: Subject to any disclaimer, the term of this patent is extended or adjusted under 35 U.S.C. 154(b) by 1157 days.

(21) Appl. No.: 10/550,685

(22) PCT Filed: Mar. 26, 2004

(86) PCT No.: PCT/DK2004/000217
§ 371 (c)(1),
(2), (4) Date: Sep. 1, 2006

(87) PCT Pub. No.: WO2004/084869
PCT Pub. Date: Oct. 7, 2004

(65) Prior Publication Data
US 2007/0042044 A1    Feb. 22, 2007

(30) Foreign Application Priority Data
Mar. 26, 2003 (DK) .................. 2003 00464
Nov. 7, 2003 (DK) .............. PCT/DK03/00765

(51) Int. Cl.
*A61K 9/36*        (2006.01)
*A61K 9/22*        (2006.01)
*A61K 9/28*        (2006.01)
*A61K 9/24*        (2006.01)
*A61K 31/40*       (2006.01)

(52) U.S. Cl. ........ 424/480; 424/472; 424/473; 424/474; 424/486; 424/488; 514/411

(58) Field of Classification Search .................... None
See application file for complete search history.

(56) References Cited

U.S. PATENT DOCUMENTS

| | | | |
|---|---|---|---|
| 3,957,523 A | 5/1976 | Ohno et al. | |
| 4,330,338 A | 5/1982 | Banker | |
| 4,389,393 A | 6/1983 | Schor et al. | |
| 4,844,984 A | 7/1989 | Eckenhoff et al. | |
| 4,873,080 A | 10/1989 | Brickl et al. | |
| 4,892,742 A | 1/1990 | Shah | |
| 5,068,112 A | 11/1991 | Samejima et al. | |
| 5,102,668 A | 4/1992 | Eichel et al. | |
| 5,213,808 A | 5/1993 | Bar-Shalom et al. | |
| 5,419,917 A | 5/1995 | Chen et al. | |
| 5,422,123 A | 6/1995 | Conte et al. | |
| 5,741,524 A | 4/1998 | Staniforth et al. | |
| 6,267,985 B1 * | 7/2001 | Chen et al. | 424/451 |
| 6,488,962 B1 | 12/2002 | Berner et al. | |
| 6,534,085 B1 * | 3/2003 | Zeligs | 424/451 |
| 6,543,085 B2 * | 4/2003 | Holsten et al. | 15/410 |
| 6,562,375 B1 | 5/2003 | Sako et al. | |
| 6,709,678 B2 | 3/2004 | Gruber | |
| 6,787,156 B1 | 9/2004 | Bar-Shalom | |
| 2001/0036959 A1 | 11/2001 | Gabel et al. | |
| 2002/0054911 A1 | 5/2002 | Oh | |
| 2003/0035836 A1 | 2/2003 | Shanghvi et al. | |
| 2004/0234602 A1 | 11/2004 | Fischer et al. | |
| 2004/0253310 A1 * | 12/2004 | Fischer et al. | 424/472 |
| 2005/0019399 A1 | 1/2005 | Fischer et al. | |
| 2005/0019405 A1 | 1/2005 | Bar-Shalom | |
| 2005/0089569 A1 * | 4/2005 | Bar-Shalom | 424/468 |
| 2005/0163837 A1 | 7/2005 | Boehm et al. | |
| 2007/0003617 A1 * | 1/2007 | Fischer et al. | 424/468 |
| 2008/0234352 A1 | 9/2008 | Fischer et al. | |
| 2008/0254122 A1 | 10/2008 | Fischer et al. | |
| 2008/0254123 A1 | 10/2008 | Fischer et al. | |
| 2008/0254124 A1 * | 10/2008 | Bar-Shalom | 424/486 |
| 2008/0268057 A1 * | 10/2008 | Andersen et al. | 424/486 |
| 2009/0274759 A1 | 11/2009 | Bar-Shalom et al. | |

FOREIGN PATENT DOCUMENTS

| | | |
|---|---|---|
| DE | 2332484 | 6/1972 |
| DE | 2415490 | 4/1973 |
| EP | 0 908 181 | 4/1999 |
| EP | 0 335 560 | 1/2002 |
| EP | 1 371 360 | 5/2005 |
| GB | 1 430 684 | 3/1976 |
| GB | 2170104 | 7/1986 |
| GB | 2182559 | 5/1987 |

(Continued)

OTHER PUBLICATIONS

The Handbook of Pharmaceutical Excipients (1988); p. 207 (Poloxamer).*
Dubbs et al.; J. of Chem. Eng. Data 1998, 43, 590-591.*
Handbook of Pharmaceutical Excipients, American Pharmaceutical Assoc. (1986): pp. 177-180 (Mannitol); 207-208 (Poloxamer) and 328-330 (Titanium Dioxide).*
Merck Index (9th Edition): Entry No. 9681 for Vitamin E.*
http://en.wikipedia.org/wiki/Phosphoric_acid (downloaded May 10, 2012).*
U.S. Appl. No. 11/915,655, filed Nov. 27, 2007, Bar-Shalom et al.
Bravo et al., "In-vitro studies of diclofenac sodium controlled-release from biopolymeric hydrophilic matrices," *J. Pharmaceutical Science*, 5(3):213-219 (2002).

(Continued)

*Primary Examiner* — Robert A Wax
*Assistant Examiner* — Jeffrey T Palenik
(74) *Attorney, Agent, or Firm* — Foley & Lardner LLP

(57) ABSTRACT

A controlled release pharmaceutical composition for oral use is provided in the form of a coated matrix composition, the matrix composition comprising i) a mixture of a first and a second polymer that have plasticizing properties and which have melting points or melting intervals of a temperature of at the most 200° C., the first polymer being selected from the group consisting of polyethylene glycols and polyethylene oxides, and the second polymer being selected form block copolymer of ethylene oxide and propylene oxide including poly(ethylene-glycol-b-(DL-lactic acid-co-glycolic acid)-b-ethylene glycol (PEG-PLGA PEG), poly((DL-lactic acid-co-glycolic acid)-g-ethylene glycol) (PLGA-g-PEG), poloxamers and polyethylene oxide-polypropylene oxide (PEO-PPO), ii) a therapeutically, prophylactically and/or diagnostically active substance, the matrix composition being provided with a coating having at least one opening exposing at one surface of said matrix, wherein the active substance is released with a substantially zero order release.

84 Claims, 10 Drawing Sheets

FOREIGN PATENT DOCUMENTS

| | | | |
|---|---|---|---|
| JP | 60/255719 | | 12/1985 |
| JP | 07/100191 | | 4/1995 |
| WO | WO 86/04817 | | 8/1986 |
| WO | WO 89/09066 | * | 10/1989 |
| WO | WO 90/08536 | | 8/1990 |
| WO | WO 91 04015 | | 4/1991 |
| WO | WO 92/09270 | | 6/1992 |
| WO | WO 95/22962 | * | 8/1995 |
| WO | WO 95/22962 A | | 8/1995 |
| WO | WO 99/44591 | | 9/1999 |
| WO | WO 99/51208 | | 10/1999 |
| WO | WO 01/35958 | | 5/2001 |
| WO | WO 01/51035 | | 7/2001 |
| WO | WO 01/51036 | | 7/2001 |
| WO | WO 01/74357 A | | 10/2001 |
| WO | WO 02/065834 | | 8/2002 |
| WO | WO 02/092078 | | 11/2002 |
| WO | WO 03/002440 | * | 3/2003 |
| WO | WO 03/02440 | * | 3/2003 |
| WO | WO 03/024426 A | | 3/2003 |
| WO | WO 03/024429 A | | 3/2003 |
| WO | WO 03/024430 A | | 3/2003 |
| WO | WO 03/024430 A1 | * | 3/2003 |
| WO | WO 2004/041252 A | | 5/2004 |
| WO | WO 2005/007074 | | 1/2005 |
| WO | WO 2005/027878 | | 3/2005 |

OTHER PUBLICATIONS

The Condensed Chemical Dictionary, "Mixture", 9th edition, p. 584 (1977).
Hoshi et al., "Cellulose and its Derivatives", pp. 24-25 (1992).
Miyazaki et al., "In situ-gelling gellan formulations as vehicles for oral drug delivery," *J. Control Release*, vol. 60, pp. 287-295 (1999).
Rowe et al., *Handbook of Pharmaceutical Excipients*, Pharmaceutical Presse, 4$^{th}$ edition, pp. 257-258 (2003).
WWW.WIKIPEDIA.ORG, web page on phosphoric acid.
Yamakita et al., "In Vivo Evaluation of Two Series of TA-5707F Controlled Release Matrix Tablets Prepared with Hydroxypropyl Methyl Cellulose Derivatives with Enter0-Soluble or Gel Formation Properties," *Biological and Pharmaceutical Bulletin*, 18(10);1409-1416 (1995).
Office Action issued Aug. 3, 2006 in U.S. Appl. No. 10/490,169 (US 2004/0253310).
Office Action issued Mar. 2, 2007 in U.S. Appl. No. 10/490,169 (US 2004/0253310).
Office Action issued Dec. 20, 2007 in U.S. Appl. No. 10/827,521 (US 2005/0019405).
Office Action issued Jul. 25, 2006 in U.S. App. No. 10/490,308 (US 2004/0234602).
Office Action issued Mar. 9, 2007 in U.S. Appl. No. 10/490,308 (US 2004/0234602).
Office Action issued Oct. 3, 2006 in U.S. Appl. No. 10/490,170 (US 2005/0019399).
Office Action issued May 9, 2007 in U.S. Appl. No. 10/490,170 (US 2005/0019399).
Office Action issued Oct. 22, 2002 in U.S. Appl. No. 09/647,590.
Office Action issued May 11, 2001 in U.S. Appl. No. 09/647,590.
Office Action issued Jul. 14, 2003 in U.S. Appl. No. 09/647,590.
Office Action issued Jan. 30, 2002 in U.S. Appl. No. 09/647,590.
Office Action issued May 14, 2008 in U.S. Appl. No. 10/845,522 (US 2007/0042044).
Office Action issued Jun. 16, 2006 in U.S. Appl. No. 10/845,522 (US 2007/0042044).
Office Action issued Oct. 27, 2005 in U.S. Appl. No. 10/845,522 (US 2007/0042044).
Office Action issued Jul. 29, 2005 in U.S. Appl. No. 10/845,522 (US 2007/0042044).
Office Action issued Mar. 21, 2007 in U.S. Appl. No. 10/845,522 (US 2007/0042044).
Office Action issued Dec. 15, 2008 in U.S. Appl. No. 12/213,087 (US 2008/0254124).
Office Action issued Jun. 16, 2009 in U.S. Appl. No. 10/550,453 (US 2007/0003617).
Office Action issued Jan. 13, 2009 in U.S. Appl. No. 10/845,522 (US 2007/0042044).
Office Action issued Apr. 29, 2009 in U.S. Appl. No. 12/076,105 (US 2008/0268057).
Office Action issued Sep. 29, 2009 in U.S. Appl. No. 12/076,105 (US 2008/0268057).
Marvola et al., "Enteric polymers as binders and coating materials in multiple-unit site-specific drug delivery systems," *European Journal of Pharmaceutical Sciences*, vol. 7, pp. 259-267, 1999.
Varshosaz et al., "Use of enteric polymers for production of microspheres by extrusion-spheronization," *Pharmaceutica Acta Helvetiae*, vol. 72, pp. 145-152, 1997.
Office Action issued on Apr. 13, 2010 in U.S. Appl. No. 10/550,453 (US 2007/0003617).
Office Action issued on Nov. 10, 2009 in U.S. Appl. No. 10/550,453 (US 2007/0003617).
Office Action issued on Nov. 4, 2009 in U.S. Appl. No. 10/845,522 (2005/0089569).
Office Action issued on Jun. 18, 2010 in U.S. Appl. No. 12/076,105 (2008/0268057).
Office Action issued on Apr. 5, 2010 in U.S. Appl. No. 12/076,105 (2008/0268057).

* cited by examiner

MATRIX COMPOSITIONS FOR CONTROLLED DELIVERY OF DRUG SUBSTANCES

FIELD OF THE INVENTION

The present invention relates to novel matrix compositions that are suitable for use in the pharmaceutical field especially for delivery of one or more active substance after oral administration.

BACKGROUND OF THE INVENTION

During the last decades many different systems for modifying the release of an active drug substance from a pharmaceutical composition have been developed. Most of them aim at obtaining a zero or a first order release rate of the active substance from the composition. Zero order release rate (i.e. constant release of the active substance with time) seems to be very difficult to obtain from a pharmaceutical composition. The present invention is based on a polymeric matrix composition, which is construed to deliver the active substance in a zero order release manner. The present invention is a further development based on the Applicant's previously described drug delivery systems, see e.g. EP-B-0 406 315, EP-B-0 493 513, EP-B-0 740 310 and WO 99/51208 the disclosure of which is hereby incorporated by reference.

It is known to obtain a controlled release of an active substance e.g. by embedding it in a polyethylene glycol matrix, cf. WO 99/51208, EP-B-0 493 513 and EP-B-0 746 310 (to the same Applicant). However, one of the challenges that still need to be solved is to provide pharmaceutical compositions for e.g. slightly soluble drug substances, wherein the pharmaceutical composition after oral administration leads to an improved bioavailability compared to known compositions. Many crystalline, therapeutically active substances have a very slight solubility in aqueous medium such as, e.g., body fluids. It is well known that changing a crystalline compound into its amorphous state will substantially increase the aqueous solubility of the compound. Accordingly, during the last decades many attempts have been made to provide compositions having the active substance present in an amorphous form. However, the amorphous form is normally not a thermodynamically stable form and, accordingly, precipitation of the crystalline form may occur during storage. The present invention addresses the above-mentioned problems.

DESCRIPTION OF THE INVENTION

For controlled release formulation solid dispersions or solid solutions offer an attractive means of increasing the solubility, and therefore, potentially, increasing the oral bioavailability of different compounds. There are several potential mechanisms by which a solid dispersion may lead to dissolution enhancement. These can be classified as a) reduction in the drug particle size, 2) changes in the surface characteristics of the drug particles to improve wet ability, and 3) formation of a higher energy solid state form (e.g. amorphous) of the active ingredient.

Accordingly, the primary reason to develop a solid molecular dispersion (amorphous form) is to enhance dissolution and improve the oral bioavailability of a poorly water-soluble drug. However, the re-crystallization of amorphous solids, their greater hygroscopicity, and their reactivity can cause difficulties in developing stable compositions. The increase in water uptake results from the ability of amorphous solids to absorb water into their internal structure, as opposed to the surface adsorption shown by denser crystalline compounds. Accordingly, in some circumstances it can be an advantage to be able to control the degree of amorphous material in the solid composition relative to the crystalline phase and at the same time obtain the desired release pattern of the formulation. With the desired release pattern according to the invention is meant controlled release such as zero order release, pulsatile or burst releases as well as immediate release.

According to the present invention a specific combination of PEO and a block copolymer such as poloxamer has shown to enable the control of amorphous and/or amorphous/crystalline phase and controlled release of an active substance from the polymer matrix system.

In the present context, the term "PEO" embraces polyethylene oxides as well as polyethylene glycols.

The present invention relates to a novel matrix composition that has been designed so that it is especially suitable in those situation where an improved bioavailability is desired and/or in those situation where a slightly or insoluble active substance is employed. Accordingly, the invention provides a controlled release pharmaceutical composition for oral use in the form of a coated matrix composition, the matrix composition comprising i) a mixture of a first and a second polymer that have plasticizing properties and which have melting points or melting intervals of a temperature of at the most 200° C., the first polymer being selected from the group consisting of polyethylene glycols and polyethylene oxides, and the second polymer being selected from block copolymer of ethylene oxide and propylene oxide including poly(ethylene-glycol-b-(DL-lactic acid-co-glycolic acid)-b-ethylene glycol (PEG-PLGA PEG), poly((DL-lactic acid-co-glycolic acid)-g-ethylene glycol) (PLGA-g-PEG), poloxamers and polyethylene oxide-polypropylene oxide (PEO-PPO), ii) a therapeutically, prophylactically and/or diagnostically active substance, the matrix composition being provided with a coating having at least one opening exposing at one surface of said matrix, the coating comprising i) a first cellulose derivative which has thermoplastic properties and which is substantially insoluble in the aqueous medium in which the composition is to be used, and at least one of ii) a second cellulose derivative which is soluble or dispersible in water, iii) a plasticizer, and iv) a filler, wherein the active substance is released with a substantially zero order release.

Matrix Composition

The pharmaceutical composition according to the invention comprises a matrix composition comprising a first polymer comprising PEO, a second polymer as described above and, one or more active substances.

Polymers

In a specific embodiment, the polymer is a substantially water soluble or crystalline polymer or a mixture of substantially water soluble and/or crystalline polymers.

The mixture of the first and the second polymer is important and provides the suitable properties of the matrix composition. As it appears from the following discussion, the block copolymer may serve as a solubilizing agent for the active substance to ensure that a certain degree of the active substance is present in the matrix composition in the desired form. The mixture of the first and the second polymer is also important as this mixture forms a dispersion medium or a solvent for the active substance. The preparation of a composition according to the invention is suitable done by heating a mixture of the two polymers together so that it becomes a melt and in this melt, the active substance is dissolved or dispersed. In the following is given more details with respect to suitable first and second polymers.

The first polymer is a polyethylene glycol and/or a polyethylene oxide. Polyethylene glycols (which when the molecular weight is above about 100,000 is denoted polyethylene oxides) are mixtures of condensation polymers of ethylene glycol. The polymers have the general formula $H(OCH_2CH_2)_nOH$ where n is an integer higher than or equal to 4. In general, each PEG is followed by a number, which corresponds to its average molecular weight.

The PEOs suitable for use according to the invention has a molecular weight of at least about 20,000 in crystalline and/or amorphous form or a mixture such polymers. It has typically a molecular weight of from about 20,000 daltons, such as, e.g., from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, such as, e.g. about 35,000 daltons, about 50,000 daltons, about 75,000 daltons, about 100,000 daltons, about 150,000 daltons, about 200,000 daltons, about 250,000 daltons, about 300,000 daltons or about 400,000 daltons.

In a preferred embodiment of the invention, the first polymer has a molecular weight of about 35,000 daltons, about 50,000 daltons, about 100,000 daltons, and about 200,000 daltons.

Mixtures of PEG with different average molecular weights can be used in order to obtain a PEG with a desirable average molecular weight. It is important to note that in such cases it is necessary to use the PEG, which have MW closest to the desired molecular weight. The individual amount of the two PEG necessary to obtain a PEG with a desired MW can be calculated from the hydroxyl number and the equation given above.

As mentioned above, a suitable process for the preparation of a composition according to the invention is by heating (suitable processes are e.g. injection moulding and extrusion) and therefore it is important that the polymers employed melt a temperature that is suitable for such processes and at the same time the temperature should not be so high that there is a risk that the active substance will undergo degradation during the manufacturing process. Accordingly, the first polymer typically has a melting point of about 20-120° C. such as, e.g. from about 30 to about 100° C. or from about 40 to about 80° C.

The first polymer is generally present in a larger amount than the second polymer. Thus, the concentration of the first polymer in the matrix composition may be from about 10 to about 99.5% such as, e.g., from about 20 to about 99%, from about 30 to about 99% w/w, from about 35 to about 95% w/w, from about 35 to about 90% w/w, from about 35 to about 85% w/w, from about 35 to about 80% w/w, from about 40 to about 75% w/w, from about 45 to about 70% w/w, from about 45 to about 65% w/w. from about 55 to about 85% w/w or from about 60 to about 85% w/w.

The second polymer is normally a polymer that has a lower molecular weight compared to the first polymer. In general, the second polymer has a hydrophilic and a hydrophobic building block so as to enable a link between a hydrophilic (e.g. the first polymer and/or a body fluid) and a hydrophobic environment (e.g. a lipophilic drug substance). The molecular weight of the second polymer is at least about 2,000 daltons.

As mentioned above, an important issue is to obtain conditions in the composition that favors the dissolution of the active substance in the composition. Hereby it is believed that the balance between the crystalline and the amorphous state of the active substance is favored with respect to the amorphous state, i.e. an improved stability is obtained.

To this end, the present inventors have found especially suitable polymeric substances that have this solubilizing effect. It is important that such a solubilizer is compatible with the polymeric material used as matrix material in order to avoid or reduce a possible phase separation and thereby increasing the risk of re-crystallization of the active substance. Examples of suitable matrix compatible solubility increasing agents are block copolymers such as e.g. water-soluble polymers like poloxamers.

Especially in polymer systems comprising polymers with the ability to form crystalline structures such as in system containing PEO, a phase separation could favor reorganization of the molecules of the active substance into crystals. Selected agents appear to be able to interact with or adhere to interfaces in the polymer system and thereby preventing the molecular interactions necessary for forming crystalline structures. The mechanism of this prevention may be obtained through sterical hindering and/or adhesion to the matrix polymer—maybe partly by a surfactant property of a solubility increasing agent. In other words, matrix compatible agents, including polymers, such as poloxamer, can reduce the speed of transition of the active substance from an amorphous state to a crystalline phase by preventing the polymer carrier to re-crystallize and thereby precipitating the active substance.

In an especially preferred embodiment of the invention, the second polymer contains ethylene glycol as a hydrophilic building block and a propylene glycol as a hydrophobic building block.

Poloxamers are copolymers or block copolymers and are a range of non-ionic surfactants of ethylene oxide (EO) and propylene oxide (PO). The composition can be an PO block flanked by polyethylene oxide chain, generating two primary functional hydroxyls or a reversed structure, where a central EO block is sandwiched between a polypropylene glycol group, resulting in an overtone of secondary hydroxyl end groups.

In chemical abstracts Diol EO/PO block copolymers are described under the scientific name—hydroxy-hydroxypoly (oxyethylene)poly(oxypropylene)-poly(oxyethylene)-block copolymer in combination with the CAS register number.

Such a polymer is a poloxamer that has the formula $HO(C_2H_4O)_a(C_3H_6O)_b(C_2H_4O)_aH$, and a is an integer from about 10 to about 150 such as, e.g., from about 30 to about 140, from about 50 to about 100, from about 65 to about 90, from about 70 to about 90 and b is an integer from about 10 to about 80 such as, e.g., from about 15 to about 80, from about 20 to about 60, from about 25 to about 55. The poloxamer for use according to the invention has a molecular weight of from about 2,000 daltons to about 20,000 daltons such as, e.g., from about 4,000 daltons to about 15,000 daltons or from about 6,000 daltons to about 10,000 daltons.

Examples of specific block-copolymers suitable for use in a composition of the invention are:

Poloxamer 101, Poloxamer 105, Poloxamer 108, Poloxamer 123, Poloxamer 124, Poloxamer 181, Poloxamer 182, Poloxamer 184, Poloxamer 185, Poloxamer 188, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407.

Poloxamers are sold under the trademark Pluronic® or Lutrol®.

The melting point of the second polymer is also of importance, although not that important as the first polymer due to the fact that the first polymer normally is present in a higher concentration than the second polymer. Normally, a suitable second polymer for use according to the invention has a melting point of about 20-120° C. such as, e.g. from about 30 to about 100° C. or from about 40 to about 80° C.

In specific embodiments a suitable poloxamer for use in a composition of the invention has a HLB value of at least about 18 such as, e.g., at least about 20. The mean molecular weight of a suitable poloxamer is typically at least about 2,000.

The concentration of the second polymer in the matrix composition is from about 0.5% to about 95% w/w such as, e.g., from about 1% to about 90% w/w, from about 5% w/w to about 90% w/w, from about 10% to about 90% w/w, from about 10% to about 80% w/w, from about 10% to about 70% w/w, from about 10% to about 60%, from about 10% to about 50%, from about 15% to about 50% w/w, from about 10% to about 45% w/w, from about 10% to about 40% w/w, from about 15% to about 40% w/w, from about 15% to about 35% w/w or from about 15% to about 30% w/w.

In embodiments where the matrix composition comprises a PEO and a poloxamer the weight ratio (PEO/poloxamer) is in a range from about 10:0.1 to about 0.1:10 such as, e.g., from about 10:1 to about 1:10, from about 5:1 to about 1:5 or from about 3:1 to about 1:3.

The release of the active substance from a composition according to the invention follows zero order kinetics at least up to release of about 50% such as, e.g., at least up to release of about 60%, at least up to release of about 70% or at least up to release of about 80% of the active substance. In particular, it has surprisingly been found that it is possible to obtain zero order release from a polymeric matrix composition without any content of e.g. like PEG 400 monostearate or PEG 2000 monostearate that has been contemplated to function as a so-called repair medium. Such a repair medium has a substantially hydrophilic domain, which gives it affinity to the (crystalline) polymeric phase, thereby filling in domains between grains and cracks in the polymer matrix and reducing the water affinity of these domains and in the polymer matrix itself. Water diffusion in the interface between the polymer crystals is thereby substantially eliminated, thus substantially limiting diffusion of water into the composition to the surface layer of the matrix, so that erosion of the composition is predominantly effected by the dissolving action of the aqueous phase on a surface or surfaces of the composition exposed to the aqueous medium. In other words a repair medium seems to prevent the diffusion of water in the polymer matrix composition.

However, surface-active substances with relative high HLB values of above about 20 are not contemplated to be able to protect the gaps and cracks from water penetration. In certain cases, the present inventors have observed that inclusion of surface active agent such as PEG monostearate 2000 has a negative impact on the mobility and/or stability of the polymer release system with respect to dissolution stability.

The present inventors have found that it is possible to obtain a zero order release from a polymer matrix composition although water may be able to diffuse into the matrix. When water diffuse into the polymer matrix composition a resulting boundary layer (or swelling layer) can be formed at the surface of the matrix composition, which is exposed to the aqueous medium. In general the diffusion of an active substance through such a boundary layer is important for the release of an active substance and, accordingly, the thickness of the boundary layer is important for the release rate. However, the present inventors have found that it is possible to eliminate or substantially eliminate the impact of the boundary layer on the release rate of the active substance from a polymer matrix composition by ensuring that the thickness of the boundary layer is relatively small and/or that the release of the active substance from a polymer matrix composition is governed by erosion of the composition and the diffusion of the active substance through the boundary layer, if any, has no or only a small impact on the overall release rate.

The present inventors have found that when water is allowed to diffuse into a polymer matrix composition zero order release is obtained when the release rate is governed or controlled by erosion of a constant surface area per time unit. In order to ensure that the erosion of the polymer matrix composition is the predominant release mechanism, the inventors have found that it is necessary to provide a polymer matrix composition which has properties that ensures that the diffusion rate of water into the polymer matrix composition substantially corresponds to the dissolution rate of the polymer matrix composition into the aqueous medium. Thus, by adjusting the nature and amount of constituents contained in the polymer matrix composition along this line the present inventors have obtained polymer matrix compositions, which release the active substance by a zero order release mechanism. The compositions employed are coated in such a manner that at least one surface is exposed to the aqueous medium and this surface has a substantially constant or controlled surface area during erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period.

A matrix composition (and pharmaceutical composition) according to the present invention is especially suitable for use in order to improve the bioavailability of a drug substance. It is also suitable for use a solvent or dispersion medium for drug substance and accordingly providing a solid solution or a solid dispersion. In the pharmaceutical technology (and in the present context), the term "solid dispersion" also embraces semi-solid dispersions. By the term is understood the finely dispersed distribution of one or more solids, e.g. an active substance like carvedilol, in an inert solid or semi-solid carrier. The active substance may be present in molecular dispersed form, i.e. as a solid solution, in fine crystalline dispersed form, in a glassy amorphous phase or dispersed as a fine amorphous powder. Eutectic mixtures, i.e. crystalline structures of active substances and carriers are also encompassed in the definition of "solid dispersions". Normally, the mean particle size is used to classify dispersed system. A colloidal dispersion is when the dispersed phase has a particle size between about 1 and about 1000 nm and a coarsely dispersion has a mean particle size of at least about 1000 nm and a molecular dispersion has a particle size below about 1 nm. Combinations between the various states are very likely and the most dominating character can be determined by X-ray diffraction spectra or differential thermoanalysis.

In a pharmaceutical composition according to the invention some of the active substance may be present in a molecular dispersion such as, e.g., in the form of a solid or semi-solid solution.

Typically, however, a pharmaceutical composition according to the invention contains the active substance on amorphous form in a colloidal dispersion or in a molecular dispersion.

Crystals or crystalline forms of the active substance may at the most partially be present in a composition of the invention. By storage of the composition it is contemplated that some re-crystallization may occur—which is acceptable as long as it has no or only minor influence of the pharmaceutical properties of the composition (dissolution data and bioavailability of the composition).

In a preferred aspect of the invention, a composition comprises the active substance that at least partially is present in amorphous form with a mean particle size of at least about 0.01 µm such as, e.g., from about 0.01 µm to about 500 µm, from about 0.05 µm to about 500 µm, from about 0.1 µm to about 500 µm, from about 0.5 µm to about 500 µm, about 1 µm to about 500 µm, typically from about 0.5 µm to about 300 µm, more typically from about 1 µm to about 200 µm, especially from about 1 µm to about 100 µm.

Active Substances

A composition according to the invention and the concept of obtaining a stable composition comprising a solid dispersion of the active substance can also be applied to other active substances than e.g. slightly soluble substances. A pharmaceutical composition according to the invention comprises one or more active substances, i.e. substances, which are therapeutically, prophylactically, diagnostically and/or biologically active substance. The term "active substance" as used herein broadly includes any compound, or mixture thereof, that can be delivered from the composition to produce a beneficial result.

As discussed above, a composition of the present invention is especially suitable for incorporation of crystalline active substances that are convertible into an amorphous form by gentle heating and at the same time have limited water solubility. However, there may be situations where it is desirable to employ other active substance such as, e.g. more water-soluble active substance. The following lists encompass both water-soluble and less water-soluble active substances.

The active and beneficial agents include pesticides, herbicides, germicides, biocides, algicides, rodenticides, fungicides, insecticides, antioxidants, plant hormone promoters, plant growth inhibitors, preservatives, disinfectants, sterilization agents, catalysts, chemical reactants, fermentation agents, food supplements, nutrients, cosmetics, therapeutically active substances (drugs), vitamins, sex sterilants, fertility inhibitors, fertility promoters, air purifiers, microorganism attenuators, ecological agents and other agents that benefit the environment in which they are used.

In the present context the term "drug substance" includes any physiologically or pharmacologically active substance that produces a localized or systemic effect in animals, in particular in mammals, including humans and primates. Other animals include domestic household, sport or farm animals such as sheep, goats, cattle, horses and pigs, laboratory animals such as mice, rats and guinea pigs, fishes, avians, reptiles and zoo animals. The term "therapeutically, prophylactically and/or diagnostically active substance" includes the term drug substance within its meaning.

In the present context, the term "ecological agent" denotes a non-therapeutic substance that has a biological effect on plants or animals in the environment. An ecological agent may be a pesticide, such as an insecticides or herbicide, a fertilizer a pheromone, a plant growth hormone or the like.

The active substance or substances included in a pharmaceutical composition of the invention may be selected from many therapeutic categories, in particular from substances which may advantageously be administered orally, rectally, vaginally, or administered to a body cavity (e.g. the urinary bladder, kidney pelvis, the gall bladder, the uterus, a central nervous system cavity, infectious/malignant/post-operative cavities, etc.).

Examples of such substances are hypnotics, sedatives, tranquilizers, anti-convulsants, muscle relaxants, analgesics, anti-inflammatory, anaesthetics, anti-spasmodics, anti-ulcer-agents, anti-parasitics, anti-microbials, anti-fungal, cardiovascular agents, diuretics, cytostatics, anti-neoplastic agents, anti-viral agents, anti-glaucoma agents, anti-depressants, sympathomimetics, hypoglycaemics, diagnostic agents, anti-cough, physic energizers, anti-parkinson agents, local anesthetics, muscle contractants, anti-malarials, hormonal agents, contraceptives, anorexic, anti-arthritic, anti-diabetic, anti-hypertensive, anti-pyretic, anti-cholingergic, bronchodilator, central nervous system, inotropic, vasodilator, vasoconstrictor, decongestant, hematine, iron salts and complexes, electrolyte supplement, germicidal, parasympathetolytic, parasympathethomimetic, antiemetic, psychostimulant, vitamin, beta-blockers, H-2 blocker, beta-2 agonist, counterirritants, coagulating modifying agents, stimulants, anti-hormones, drug-antagonists, lipid-regulating agents, uricosurics, cardiac glycosides, ergots and derivatives thereof, expectorants, muscle-relaxants, anti-histamines, purgatives, contrast materials, radiopharmaceuticals, imaging agents, anti-allergic agents.

Examples of specific active substances suitable for use in a composition of the invention are:

Carvedilol, morphine, diclofenac, nifedipine, calcitonin, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecainide, alprenolol, propoanolol, nadolol, pindolol, oxprenolol, labetalol, timolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephadroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, tinidazole, trimethoprim, norfloxacin, salazosulfapyridin, aminosalyl, isoniazid, etambutol, nitrofurantoin, nalidixic acid, metanamine, chloroquin, hydroxichloroquin, tinidazol, ketokonazol, acyclovir, interferon idoxuridin, retinal, tiamin, dexpantenol, pyridoxin, folic acid, ascorbic acid, tokoferol, phytominadion, phenfluramin, corticotropin, tetracosactid, tyrotropin, somatotoprin, somatrem, vasopressin, lypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityidion, meprobamat, chlordiazepoxid, diazepam, nitrazepam, baclofen, oxazepam, dikaliumclorazepat, lorazepam, flunitrazepam, alprazolam, midazolam, hydroxizin, dantrolene, chlometiazol, propionmazine, alimemazine, chlorpromazine, levomepromazine, acetophenazine, fluphenazine, perphenazine, prochlorperazine, trifluoperazine, dixyrazine, thiodirazine, periciazin, chloprothixene, tizanidine, zaleplon, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenytoine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfiram, morphine, codeine, pentazocine, buprenorphine, pethidine, phenoperidine, phentanyl, methadone, piritramide, dextropropoxyphene, ketobemidone, acetylsalicylic acid, celecoxib, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, ornidazol, tinidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, sulfonylurea, mefformin, insulin, calcitonin, glucagons-like peptide-1.

The active substance can be in various forms, such as uncharged or charged molecules, molecular complexes, crystalline forms, amorphous forms, polymorphous form, solvates, anhydrates, and pharmaceutically acceptable salts such as a hydrochloride, hydrobromide, sulfate, laurylate, palmitate, phosphate, nitrite, nitrate, borate, acetate, maleate, tartrate, oleate, and salicylate. For acidic active substance, salts of metals, amines amino acids or organic cations, quaternary ammoniums, can be used. Derivatives of active substances such as esters, ethers and amides which have solubility characteristics suitable for use herein can be used alone or mixed with other drugs. After release of the derivative from the composition it may be converted by enzymes, hydrolysed by body pH or other metabolic processes to the parent drug or to another biologically active form.

A pharmaceutical composition of the invention may in addition be suitable for the delivery of polypeptides, for example hormones, enzymes such as lipases, proteases, carbohydrates, amylases, lactoferrin, lactoperoxidases, lysozymes, nanoparticles, etc., and antibodies. The composition may also be employed for the delivery of microorganisms, either living, attenuated or dead, for example bacteria, e.g. gastrointestinal bacteria such as streptococci, e.g. *S. faecium, Bacillus* spp. such as *B. subtilis* and *B. licheniformis*, lactobacteria, *Aspergillus* spp., bifidogenic factors, or viruses such as indigenous vira, enterovira, bacteriophages, e.g. as vaccines, and fungi such as baker's yeast, *Saccharomyces cerevisiae* and fungi imperfecti. A pharmaceutical composition of the invention may also be used for the delivery of active agents in specialized carriers such as liposomes, cyclodextrines, nanoparticles, micelles and fats.

A further use for which a composition of the invention is suited is the delivery of active substances to animals. Examples of such active substances for veterinary use are antiparasitics, corticosteroids, antibiotics, antiimflammatory agents, growth promoters and permittants, antifungals and antihelmintics.

Many active substances present polymorphism, i.e. several different crystalline forms exist. As the different forms of crystals may present different stability properties with respect to temperature, pressure, moisture, etc., and some forms may be metastable and the more stable forms tend to be less soluble, it is desirable to convert and preserve the crystallized bulk active substance into an amorphous state in the pharmaceutical composition.

The present invention demonstrates that in order to obtain a composition capable of releasing the active substance with a zero order release pattern having the same release rate in both acidic and in basic environment so as to maintain a predictable release in the patient despite possible variations in retention times in the stomach, it is important that the dispersion medium, i.e. the matrix composition is carefully selected in order to avoid an unpredicted behaviour of the composition when it comes to erosion of the composition and release of the active substance.

In those cases where the active substance is present in the matrix composition in the form of a solid dispersion or solid solution, the present inventors have found that it is of utmost importance in order to obtain a stable composition that the active ingredient is present in the solid dispersion in a suitable concentration that makes it possible to prevent formation of any unwanted precipitates during storage under normal conditions. As already discussed herein it is especially of interest to avoid formation of crystals of the active substance.

Normally supersaturated systems (i.e. systems wherein the concentration of a given substance in a medium is larger than the solubility in the medium) are instable systems that after a certain time period will lead to precipitation of the substance in the medium. In a saturated system, which is a stable system, equilibrium between solid and dissolved substance will take place. In systems where the active substance is present in dissolved form and the concentration of the substance is well below the solubility normally no change with respect to formation of precipitates will take place (unless the substance is degraded to insoluble products etc.). A dissolved system may therefore be regarded as a stable system. However, in practice the situation is often much more complex and it is normally necessary to stabilize even dissolved system by use of different methods.

As already discussed above, it is important that a composition according to the invention releases at least most of the active substance by a zero order release mechanism. One aspect of research about controlled-release delivery systems involves designing a system, which produces steady-state plasma drug levels. The release of active substance from such systems is also referred to as zero-order drug release kinetics.

A pharmaceutical composition of the invention is designed to release the active substance in a controlled manner such as by a zero order release mechanism. Accordingly, the composition is especially suitable for a controlled release of an active substance. In the present context the term "controlled release" is used to designate a release a desired rate during a predetermined release period. Terms like "modified", "delayed", "sustained", "prolonged", "extended" etc. release are in the present context synonyms to the term "controlled release".

In an embodiment of the invention, the active substance is a pharmaceutically active powder. The powder typically has a particle size of from about 0.01 µm to about 500 µm, 0.1 µm to about 500 µm, typically from about 0.5 µm to about 300 µm, more typically from about 1 µm to about 200 µm, especially from about 5 µm to about 100 µm.

A pharmaceutical composition according to the invention is—due to the possibility of designing the composition in such a manner that i) a zero order release is obtained and ii) a controlled release during a predetermined time period is obtained—suitable for use for water soluble as well as slightly soluble or insoluble active substances. However, it is contemplated that a composition is especially suitable for use when the at least one therapeutically, prophylactically and/or diagnostically active substance has a solubility of at the most about 3 mg/ml such as, e.g. at the most about 1 mg/ml, at the most about 0.1 mg/ml, at the most about 0.05 mg/ml such as, e.g. at the most about 0.001 mg/ml in water at ambient temperature and/or a prolonged release of the active substance is desired in order to obtain i) a prolonged residence time within the body after administration, ii) a reduced peak plasma concentration in order to avoid peak related side effects, iii) reduced frequency of administration in order e.g. to obtain a better patient compliance, etc.

To this end it seems that substantially hydrophobic active substances tend to result in a decrease in the erosion rate of the matrix composition. Substantially hydrophilic or water-soluble active substances seem to have the opposite effect, i.e. they tend to result in a faster erosion of the matrix.

The at least one therapeutically, prophylactically and/or diagnostically active substance will suitably be present in an amount of up to about 60%, typically up to about 50%, by weight of the matrix composition. An active substance content of about 60% is contemplated to be the maximum content, which still allows for a sufficient content of the polymer and, when relevant, the pharmaceutically acceptable excipient in the composition. The active substance may, on the other hand, be present in the composition in much smaller amounts, depending on the nature and potency of the active substance in question.

Stability

A composition according to the invention aims at having a sufficient stability.

In the present context, the terms "stability" and "stabilizing agent" are employed to encompass one or more of the following:

Stability with respect to the final composition:

i) stability with respect to the physical stability of the composition (appearance, color, strength, etc ii) stability with respect to in vitro dissolution behavior of the active substance from the composition Stability of the individual components:

iii) stability with respect to the chemical stability of the active substance (degradation of the active substance to other—normally—unwanted products)

iv) stability with respect to the form the active substance has in the composition; normally, the active substance is dissolved (molecularly dispersed) in the polymer as a solid dispersion. In such cases precipitation or otherwise formation of crystals of the active substance in the composition is an indication of a stability problem.

v) physical and chemical stability of the pharmaceutically acceptable polymer employed as component i).

Normally, stability is considered under specific storage and test conditions. In the present context, a stable composition is a composition that does not change (with respect to a specific property) more than 20% within a time period of at least 2 weeks (when physical parameters are considered) or a period of at least 3 months (when chemical parameters are considers). Specific conditions appear from the patent claims herein.

In preferred embodiments, the physical stability is at least 3 month, such as at least 6 months and more preferred at least 9 month at storage conditions of 25° C. and at a relative humidity of 60%.

An important feature of the invention is that the active substance can be converted to and stabilized in its amorphous form as a solid dispersion. The amorphous state and/or the solid dispersion is stabilized either by a very careful choice of the concentration of the active substance in the composition and/or by addition of suitable stabilizing agents acting by stabilizing one or more of the conditions mentioned above under items i) to v).

A stabilizing agent may contribute to an improved solubility of the active substance in its crystalline and/or in any of its amorphous forms. Without being bound to any theory it may be assumed that the stabilizing agent together with the polyethylene glycol and/or the polyethylene oxide represent the dispersion medium wherein the solubility of the active substance may be higher than in the polyethylene glycol and/or polyethylene oxide. The same may apply with respect to the stability of the amorphous form of the active substance.

Accordingly, a composition according to the inventions may as a stabilizing agent contain a substance, which—together with the first and second polymer—form a dispersion medium in which the active substance is contained.

In the following is given examples of various substances that may be employed as stabilizing agents. Although they are mentioned as having a specific function they may also have other stabilizing effects on the composition and therefore, they may be employed for other stabilizing purposes as well. An example is e.g. the use of an acidic substance that is believed to have stabilizing impact on both the stability of an amorphous state of the active substance as well as impact on the dissolution behavior of the composition. The following classification of stabilizers should therefore not limit the use of the stabilizing substances to the specific function as it may as well serves other stabilizing functions as well.

The requirements of having the amorphous state of the active substance in a composition and at the same time having a composition with suitable stability also with respect to the release of the active substance from the composition can be obtained for an increased period of time by combining one or more of the following principles for the composition.

1. Adjust pH in the polymer matrix to ensure conditions for having the active substance present in dissolved form.
2. Add buffering agents to the polymer matrix in order to reduce the risk of precipitation of the active substance (e.g. as crystals) when the composition is subjected to neutral/basic media like the intestinal fluids.
3. Add matrix compatible solubility increasing agents or mixtures thereof.
4. Select one or more polymers having a relative high molecular weight within the range possible in order to obtain an erosion time that is within the desired range for the composition.
5. Include at least one heating step in the process for the preparation of the composition when the active substance and the polymer are in physical contact.
6. Increase Tg for the composition in order to have an enlarged difference between Tg and storage temperature. Suitable substances are e.g. mono, di-, oligo- or polysaccharides.

In a specific embodiment, the pharmaceutically acceptable polymer employed as component a first polymer is a polyethylene oxide having a molecular weight of at least about 20,000 in crystalline and/or amorphous form or a mixture such polymers. More details on suitable polymers are disclosed herein. The solubility of a particular active substance in PEO depends inter alia on the quality and the molecular weight of the PEO employed. Thus, in order to determine a suitable concentration of the active substance in a composition of the invention it is necessary to determine the solubility of the active substance in the PEO (or other polymers employed) in question. The solubility is normally determined at a temperature that corresponds to the melting or softening point of the PEO in question and the solubility determined is the saturation solubility. A person skilled in the art knows how to determine the solubility of a specific substance in a specific polymer.

Pharmaceutically Acceptable Excipients

In general, the stabilizing agents mentioned herein before may also be employed as pharmaceutically acceptable excipients.

Other Ingredients in the Matrix Composition

The matrix composition may also contain other excipients as well, e.g. in order to improve the technical properties of the matrix composition so that it may be easier to produce or in order to improve the stability of the composition.

A suitable pharmaceutically acceptable excipient for use in a matrix composition of the invention may be selected from the group consisting of fillers, diluents, disintegrants, glidants, pH-adjusting agents, viscosity adjusting agents, solubility increasing or decreasing agents, osmotically active agents, stabilizers, surface active agents and solvents.

Suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as acacia, sodium alginate, starch, gelatin, saccharides (including glucose, sucrose, dextrose and lactose), molasses, extract of Irish moss, panwar gum, ghatti gum, mucilage of isapol husk, carboxymethylcellulose, methylcellulose, veegum, larch arabolactan, polyethylene glycols, ethylcellulose, water, alcohols, waxes, polyvinylpyrrolidone such as, e.g., PVP K90 (may be used to improve mixing of the polymer with the other ingredients) or mixtures thereof; lubricants such as talc, magnesium stearate, calcium stearate, staeric acid, hydrogenated vegetable oils, sodium benzoate, sodium chloride, leucine, carbowax 4000, magnesium lauryl sulfate, colloidal silicon dioxide and mixtures thereof, disintegrants such as starches, clays, cellulose derivatives including crosscarmellose, gums, aligns, various combinations of hydrogencarbonates with weak acids (e.g. sodium hydrogencarbonate/tartaric acid or citric acid) crosprovidone, sodium starch glycolate, agar, cation exchange resins, citrus pulp, veegum HV, natural sponge, bentonite or mixtures thereof; volatile solvents such as alcohols, including aqueous alcohols, petroleum benzine, acetone, ether or mixtures thereof; plasticizers such as sorbitol and glycerine; and others such as cocoa butter, polyethylene glycols or polyethylene oxides, e.g. with a molecular weight of about 1,000-500,000 daltons, typically about 1,000-100,000 daltons, more typically 1,000-50,000 daltons, especially about 1,000-10,000 daltons, in particular about 1,500-5,000 daltons, and mixtures thereof, hydrogenated vegetable oils, glycerinated gelatin or mixtures thereof.

The matrix composition may in addition include a cellulose derivative, e.g. a cellulose derivative selected from the group consisting of methylcellulose, carboxymethylcellulose and salts thereof, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose. Of these cellulose derivatives, hydroxypropylmethylcellulose and methylcellulose are preferred for incorporation in the matrix composition.

Furthermore, the matrix composition may comprise one or more agents selected from the group consisting of sweetening agents, flavouring agents and colouring agents, in order to provide an elegant and palatable preparation. Examples of colouring agents are water-soluble FD&C dyes and mixtures thereof with corresponding lakes and direct compression sugars such as Di-Pac from Amstar. In addition, coloured dye migration inhibitors such as tragacanth, acacia or attapulgite talc may be added. Specific examples include Calcium carbonate, Chromium-cobalt-aluminium oxide, ferric ferrocyanide, Ferric oxide, Iron ammonium citrate, Iron (III) oxide hydrated, Iron oxides, Magnesium carbonate, Titanium dioxide.

Examples of suitable fillers are also dextrin, sucralfate, calcium hydroxyl-apatite and calcium phosphates.

The filler may be added in an amount so that the combination of the filler and the active substance comprises up to about 60%, typically up to about 50%, by weight of the first composition.

In order to soften the carrier system, a plasticiser may be incorporated in the composition. A suitable plasticizer is selected from the group consisting of phosphate esters; phthalate esters; amides; mineral oils; fatty acids and esters; fatty alcohols, vegetable oils and hydrogenated vegetable oils including acetylated hydrogenated cottonseed glyceride and acetylated hydrogenated soybean oil glycerides; acetyl tributyl citrate, acetyl triethyl citrate, Castor oil, diacetylated monoglycerides, dipropylene glycol salicylate glycerin, glyceryl cocoate, mono- and di-acetylated monoglycerides, nitrobenzene, carbon disulfide, β-naphtyl salicylate, phthalyl glycolate, diocyl phthalate; sorbitol, sorbitol glyceryl tricitrate; sucrose octaacetate; a-tocopheryl polyethylene glycol succinate, phosphate esters; phthalate esters; amides; mineral oils; fatty acids and esters; fatty alcohols; and vegetable oils, fatty alcohols including cetostearyl alcohol, cetyl alcohol, stearyl alcohol, oleyl alcohol and myristyl alcohol; methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate, butyl oleate, butyl stearate, di(beta-methoxyethyl)adipate, dibutyl sebacate, dibutyl tartrate, diisobutyl adipate, dihexyl adipate, triethylene glycol di(beta-ethyl butyrate), polyethylene glycol di(2-ethyl hexoate), diethylene glycol monolaurate, monomeric polyethylene ester, hydrogenated methyl ester of rosin, methoxyethyl oleate, butoxyethyl stearate, butyl phthalyl butyl glycolate, glycerol tributyrate, triethylene glycol dipelargonate, beta-(p-tert-amyl phenoxy)ethanol, beta(p-tert-butytphenoxy)ethanol, beta-(p-teft-butytphenoxyethyl)acetate, bis(beta-p-tert-buthylphenoxydiethyl)ether, camphor, Cumar W-1, Cumar MH-1, Cumar V-1, diamyl phthalate, (diamylphenoxy)ethanol, diphenyl oxide, technical hydroabietyl alcohol, beckolin, benzene hexahydrochlonde, Clorafin 40, Piccolastic A-5, Piccalastic A-25, Flexol B400, Glycerol alfa-methyl alfaphenyl ether, chlorinated naphthalene, HB-40, monoamylphthalate, Nevillac 10 o-nitrodiphenyl and Paracril 26.

Preferred anti-oxidative agents include TPG e.g. in the form of TPGS due to surfactant properties, BHA, BHT, t-butyl hydroquinone, calcium ascorbate, gallic acid, hydroquinone, maltol, octyl gallate, sodium bisulfite, sodium metabisulfite, tocopherol and derivates thereof, citric acid, tartaric acid, and ascorbic acid. Other antioxidants include trivalent phosphorous like e.g phosphite, phenolic antioxidants, hydroxylamines, lactones such as substituted benzofuranones. Hindered phenols, thiosynergists and/or hindered amines are useful for the long-term stability for polymers, whereas the following antioxidants are suitable for use also in situation where the active substance is subject to oxidation: acids (ascorbic acid, erythorbic acid, etidronic acid, gallic acid, hypophosphorous acid, nordihydroguairetic acid, propionic acid etc.), phenols (e.g. BHA, BHT, t-butyl hydroquinone, dodecyl gallate, octyl gallate, 1,3,5-trihydroxybenzene), organic and inorganic salts (calcium ascorbate, sodium ascorbate, sodium bisulphite, sodium metabisulfite, sodium sulfite, potassium bisulphite, potassium metabisulphite), esteres (calcium ascorbate, dilauryl thiodipropionate, dimyristyl thiodipropionate, distearyl thiodipropionate), pyranon (maltol), and vitamin E (tocopherol, D-α-tocopherol, DL-α-tocopherol, tocopheryl acetate, d-α-tocopheryl acetate, dl-α-tocopheryl acetate. However, other anti-oxidative agents known in the art may be used according to the present invention.

Other substances that may be included in the PEO/PEG/Poloxamer matrix as solubilizer and the present inventors have found that incorporation of an organic or inorganic acid favors the dissolution from the composition.

Suitable acids may be selected from the group consisting of inorganic acids, organic acids and pharmaceutically acceptable salts or complexes thereof. Mixtures thereof are also of relevance.

The acid may also be a mono-, di-, oligo, polycarboxylic acid or amino acids such as, e.g. acetic acid, succinic acid, citric acid, tartaric acid, acrylic acid, benzoic acid, malic acid, maleic acid, sorbic acid etc., aspartic acid, glutamic acid etc.

Examples of suitable organic acids include acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, and pyruvic acid.

Examples of suitable inorganic acids include pyrophosphoric, glycerophosphoric, phosphoric such as ortho and/or meta phosphoric, boric acid, hydrochloric acid, and sulfuric acid.

In a specific aspect of the invention the acidic substance is meta and/or ortho phosphoric acid.

The concentration of an acid substance in the composition is normally from about 0% w/w to about 10% w/w such as, e.g. from about 1% w/w to about 7.5% w/w or from about 2% to about 6% w/w.

pH Dependant Release

In some situations it may be convenient that the composition releases the active substance in a pH dependant manner. As described in e.g. WO 99/51208 a pH dependant release can be obtained by inclusion of a so-called release rate modifier.

The release rate modifier is preferably selected from materials conventionally used in the pharmaceutical industry to produce enteric coatings. A number of different types of compounds suitable for use as enteric coatings are known in the art; see e.g. *Remington's Pharmaceutical Sciences*, 18 h Edition, 1990. Release modifiers may in particular be selected from one of three general classes, namely cellulose derivatives, methacrylic acid polymers and modified gelatine compounds. Preferred release modifiers include cellulose acetate phthalate, polyvinyl acetate phthalate, hydroxypropyl methylcellulose phthalate and hydroxypropyl methylcellulose acetate succinate, as well as methacrylic acid copolymers. Modified gelatine compounds include gelatine treated with e.g. formaldehyde or glutaraldehyde.

Examples of commercially available polymers suitable as release modifiers are EUDRAGIT® L and EUDRAGIT® S, available from Röhm GmbH, Germany, and enteric coating agents available from Shin-Etsu Chemical Co., Japan. The release modifier will typically be present in the composition in an amount of about 0.1-10%, based on the weight of the matrix, preferably about 0.5-4%, e.g. about 1-3%, such as about 1.5-2.0%. If desired, a suitable mixture of more than one release modifier may be used in order to obtain a desired release profile in any given composition.

The release modifier enables a difference in release of the active substance/erosion of the matrix dependant on pH.

Shape

The geometric form of the composition is important for the obtainment of the above-mentioned controlled zero order. Thus, in a preferred version of the invention, the pharmaceutical composition of the invention has a geometric shape, which enables a substantially constant surface area to become exposed during erosion of the matrix. Suitable shapes are shown in e.g. EP-B-0 406 315, EP-B-0 493 513, EP-B-0 740 310 and WO 99/51208 to which reference is made.

Specific examples of compositions with different shapes and sizes are:

| Batch | Length [mm] | Diameter [mm] | Vol [mm³] |
|---|---|---|---|
| 01-0034-042 | 7.5 | 5.05 | 150 |
| 01-0035-042 | 6.0 | 5.64 | 150 |
| 01-0043-042 | 9.0 | 4.6 | 150 |

The following table describes formulations having a cylindrical form and oval openings in both ends

| Batch | Length [mm] | Vol [mm³] | Longest/shortest diameter [mm] |
|---|---|---|---|
| 01-0075-042 | 6.0 | 150 | 8.74    3.64 |
| 01-0076-042 | 7.5 | 150 | 7.82    3.21 |

The coated compositions obtained were open at two opposite ends. The area for an open end is calculates as the volume/length of the cylindrical formulations.

In a further embodiment of the invention it is possible to prepare different strength based on only one specific matrix composition.

The different strengths of the pharmaceutical composition are then prepared based on a desired specific formulation, which has shown the desired release duration. The release period is then secured by keeping the same length in each strength formulation. Simply by decreasing or increasing the exposed area with the same fold as the desired increase or decrease, respectively, in the desired strength compared to the strength of the basis formulation different. In other words, the ratio between the amount of active substance and surface area of the original basis formulation is constant in each individual strength formulation.

However, minor corrections in the calculated area for the additional strength formulations may be necessary in case the erosion rate (length of the eroded matrix/time unit) is dependent on the size of the area indicating non-linearity. However such non-linearity may be tested by measuring the erosion rate individually with two different exposed areas of the same matrix composition. In case the formulations show different dissolution rates, the ratio between the areas and the rates may be calculated.

These factors can be used to adjust the area and/or the length of the specific desired new strength when exactly the same matrix is preferred in different pharmaceutical strengths.

In vitro, it is believed that when the area is decreased, the physical factors of the dissolution parameters, (paddle rotation speed) might have a decreased erosion effect on the surface area bearing in mind the present shape of the formulation is a tube where the coat or wall of the tube remains intact during the erosion process.

Coating

The pharmaceutical composition may thus have the shape of a cylindrical rod, which is provided with a coating, which is substantially insoluble in and impermeable to fluids such as body fluids during the intended release period, the coating having an opening at one or both ends. Polymers useful as coatings are preferably those, which are possible to process by extrusion, solution or in the form of a dispersion. Most preferred are those, which are available in a food grade or a pharmaceutical grade quality. Examples of such polymers are cellulose acetate, polyamide, polyethylene, polyethylene terephthalate, polypropylenem polyurethane, polyvinyl acetate, polyvinyl chloride, silicone rubber, latex, polyhydroxybutyrate, polyhydroxyvalerate, teflon, polylactic acid or polyglycolic acid and copolymers thereof, copolymers such as ethylene vinyl acetate (EVA), styrene-butadienestyrene (SBS) and styrene-isoprene-styrene (SIS).

The coating may also be a coating, which is substantially soluble in and permeable to fluids such as body fluids during the intended release period provided that the coating dissolves so much slower than the matrix composition that the coating remains intact until the matrix has eroded and released the active substance. Examples of suitable polymers include polyols as described herein.

The coating may further comprise any of the above-mentioned matrix materials in a form, which erodes at a substantially slower rate than the rest of the matrix. The coating may thus comprise a matrix of one or more substantially water soluble crystalline polymers and, optionally, a non-ionic emulsifier, the coating being one which is eroded in the aqueous phase at a substantially slower rate than the matrix composition comprising the active substance, whereby a substantially constant area of the matrix composition comprising the active substance is exposed during erosion of the matrix composition, and whereby the coating is substantially eroded upon erosion of the matrix composition comprising the active substance. Such a coating will be designed so that its longitudinal erosion rate is substantially the same as the longitudinal erosion rate of the matrix, whereby the matrix and the coating will erode longitudinally towards the centre of the composition at substantially the same rate. Thus, when the matrix composition has been completely eroded by the aqueous medium, the coating will also be substantially completely eroded. A matrix composition having such a coating has the obvious advantage of being completely biodegraded upon release of the active substance. Such a coating will typically be a combination of a polyethylene glycol and a mixture of, for example, polyethylene glycol 400 monostearate or another non-ionic emulsifier, and may also include a filler. The content of the mixture of non-ionic emulsifiers and the filler in the coating will be determined in each particular case according to the characteristics, e.g. erosion rate and size, of the matrix comprising the active substance.

In an embodiment of the invention, the coating is one, which disintegrates or crumbles after erosion of the matrix. A coating of this type would remain intact as long as it was supported by the matrix containing the active substance, but it would lack the ability to remain intact after erosion of the matrix, whereby it would then disintegrate or crumble, so that it would not remain in e.g. a human or animal for any significant amount of time after the complete erosion of the matrix and the release of the active substance. The above-mentioned coatings are only given by way of examples and are not intended to limit the invention in any way.

The coating may also be an enteric coating employing methacrylates, a co-polymer of methacrylate-galactomannan etc.

In an interesting embodiment, the controlled release composition of the invention further comprises a coating having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled. Coatings of this type are described in WO 95/22962, to which reference is made and which is incorporated herein by reference. These coatings comprise:

(a) a first cellulose derivative which has thermoplastic properties and which is substantially insoluble in the aqueous medium in which the composition is to be used, e.g. an ethylcellulose such as ethylcellulose having an ethoxyl content in the range of 44.5-52.5%, or cellulose acetate, cellulose propionate or cellulose nitrate;

and at least one of:

(b) a second cellulose derivative which is soluble or dispersible in water, e.g. a cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose;

(c) a plasticizer, e.g. selected from the group consisting of phosphate esters; phthalate esters; amides; mineral oils; fatty acids and esters thereof with polyethylene glycol, glycerin or sugars; fatty alcohols and ethers thereof with polyethylene glycol, glycerin or sugars; and vegetable oils; or a non-ionic surfactant; and (d) a filler, e.g. selected from conventional tablet or capsule excipients such as diluents, binders, lubricants and disintegrants.

The first cellulose derivative (a) such as, e.g., ethylcellulose is typically contained in the coating in a concentration of from about 10 to about 99% w/w such as, e.g., from about 20 to about 95% w/w, from about 30 to about 90% w/w, from about 40 to about 90% w/w, from about 45 to about 90% w/w, from about 50 to about 85% w/w or from about 50 to about 80% w/w.

The use of a plasticizer will often be desirable in order to improve the processability of the ethylcellulose or the first cellulose derivative. The plasticizer may also be a non-ionic surfactant, e.g. a non-ionic surfactant selected from the group consisting of diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters; nitrobenzene, carbon disulfide, β-naphtyl salicylate, phthalyl glycolate, dioctyl phthalate.

Other suitable plasticizers appear from EP-B-0 746 310 to which reference is made. A coating of this type may in addition further comprise a release modifier of the type described above, so that the coating is provided with an erosion profile similar to that of the matrix composition in terms of the relative rate of erosion in the stomach and the intestines, respectively. In this case, it may be advantageous to incorporate a somewhat higher concentration of the release modifier in the coating than the concentration of release modifier in the matrix, so as to ensure that the coating does not erode in the stomach at a faster rate than the matrix.

Pharmaceutical Composition

As mentioned above a pharmaceutical composition according to the invention is a coated matrix composition from which the active substance is released in by a zero order release mechanism.

A composition according to the invention containing a drug substance is typically for oral administration and may be in the form of a tablet or a capsule or in the form of a multiple unit dosage form. Due to the possibility of controlling the release rate of the active substance the composition may be adapted for oral administration 1-6 times a day, normally 1-4 times daily such as 1-3 times daily. The technology may also provide compositions for administration only once or twice daily. In the present context the term "once daily" is intended to mean that it is only necessary to administer the pharmaceutical composition once a day in order to obtain a suitable therapeutic and/or prophylactic response; however, any administration may comprise co-administration of more than one dosage unit, such as, e.g. 2-4 dosage units if the amount of active substance required may not be formulated in only one composition or if a composition of a smaller size is preferred.

The dosage of the active substance depends on the particular substance, the age, weight condition etc. of the human or animal that will be treated with the composition etc. All such factors are well known to a person skilled in the art.

The controlled release of the active substance is caused by erosion at a substantially constant rate of a surface or surfaces of the first composition The rate at which the active substance is released from the matrix is a predetermined rate, i.e. a rate, which is controllable over a certain period of time.

The release rate required in each particular instance may inter alia depend on the amount of active substance to be released for it to exert the desired effect, as well as on the overall dosage of the active substance contained in the matrix. The substance of which the matrix is composed and the distribution of the active substance in the matrix may therefore be selected according to one or more of these criteria to ensure the desired level of release of the active substance.

Due to the controlled release of the active substance obtainable from the pharmaceutical composition of the invention, it is possible to obtain a substantially constant rate of release of the active substance over a specific period of time, corresponding to the dosage necessary for the treatment in question, so that adherence to a strict dosage regimen, e.g. requiring administration of a drug at set intervals up to several times a day, may be dispensed with.

Furthermore, it is possible to include two or more different active substances in the pharmaceutical composition of the invention, and the two or more different active substances may be adapted to be released at different concentrations and/or intervals, thus making it easier for patients to follow a prescribed regimen.

An additional advantage of a pharmaceutical composition of the invention, compared to other known controlled release compositions, is that it may be produced by relatively simple and inexpensive methods.

Furthermore, a pharmaceutical composition according to the invention allows for the incorporation of high concentrations of the active substance relative to the size of the delivery system. This is obviously a great advantage, notably when the composition is to be used for the delivery of a therapeutically, prophylactically and/or diagnostically active substance, since it allows for the delivery of the required amount of the active substance without the size of the composition being unnecessarily large. In addition, sparingly soluble or non-soluble active substances may be readily incorporated into a composition of the invention. A composition of the invention may thus be used for the delivery of, for example, sparingly soluble or non-soluble pharmaceutical powders which can otherwise be difficult to administer.

As mentioned above, the release of the active substance from the pharmaceutical composition corresponds to a substantially zero order release determined by in vitro dissolution test according to USP. The substantially zero order release is obtained in a time period of at least 1 hours such as, e.g. at least 2 hours, at least 3 hours, at least 4 hours or at least 5 hours, or in a time period of at least 5 hours such as, e.g. at least 6 hours, at least 7 hours, at least 8 hours, at least 9 hours or at least 10 hours.

Multiple Units Composition

The pharmaceutical composition according to the invention may furthermore be used in the preparation of a multiple units pharmaceutical composition, e.g. in the form of a capsule or tablet. A multiple units pharmaceutical composition is a composition, which comprises a multiplicity of individual units in such a form that the individual units will be made available upon disintegration of the composition, typically a capsule or tablet, in the stomach of humans or animals ingesting said composition. Thus, in this case, at least some of the individual units in said multiple units pharmaceutical composition will consist of the composition of the invention, the individual units being of a size, which allows them to be incorporated into such a composition.

Preparation

The delivery system as well as the first composition of the invention may be produced by various methods which are either known per se in the pharmaceutical industry or which, for example, are used in the production of polymer-based materials, depending upon the desired embodiment and the materials employed in the composition in question. As mentioned above, one advantage of the composition according to the invention is that it may be produced by methods, which are relatively simple and inexpensive.

It should also be mentioned that a composition of the invention is especially suitable when it is desired to have an amorphous form of the active substance in the composition, because the most convenient process for the preparation of a composition of the invention involves heating of the polymer together with the active substance and the conversion from the crystalline state to the amorphous state requires addition of energy (heating).

Normally, when preparing a composition according to the invention heating is employed for an injection moulding process. During heating it has been observed that PEO in various qualities forms free radicals that results in the formation of inter alia formaldehyde and formic acid. These products may often lead to further degradation e.g. of the active substance present in the composition and it is therefore necessary to take the necessary precautions in this respect. Oxidative free radicals degradation by hydroperoxides can be catalysed by certain transition metal ions, especially those of copper, cobalt and manganese. Thus, employment of PEO qualities devoid of or only containing a very small amount of such transition metal ions may improve stability. Another possibility is to use component ii) in a quality that ensures that free radicals formed, if any, do not significantly increase the degradation of the active substance in the composition. Such a quality could e.g. be a quality containing an antioxidant that functions by preventing the formation of free radical during heating or by scavenging any free radicals formed. Another possibility is to add such antioxidant to the formulation before any heating takes place.

Suitable qualities include PEO 200,000 NF or LF from Dow Chemicals.

A composition according to the invention may therefore further comprise one or more antioxidants that inhibits the formation of peroxides and/or inactivates any peroxides present.

Suitable antioxidants for use includes beta-caroten (a vitamin A precursor), ascorbic acid, ascorbyl palmitate, butylated hydroxyanisole, butylated hydroxytoluene, hypophosphorous acid, monothioglycerol, potassium metabisulfite, sodium metabisulfite, propyl gallate, sodium formaldehylde sulfoxylate, sodium thiosulfate, sulfur dioxide, tocopherol, tocopherol acetate, tocopherol hemisuccinate, TPGS or other tocopherol derivatives, sulfides, phosphine etc. Other suitable antioxidants are described herein.

It is believed that the amorphous state of the active substance is furthermore favoured by the processing procedures of the preparation of the product according to the present invention, which in a preferred embodiment involves injection moulding of the pharmaceutical units.

The injection moulding technique have the advantage of simultaneous mixing and heating the components during increased pressure in a one step procedure without exposure to air and moisture because the injection moulding is performed in a single closed compartment from the time the blend has entered the machine to the final pharmaceutical units are ejected ready for packaging.

In a further aspect of the invention, the blending process may be followed by an extrusion step for obtaining pellets suitable for feeding of the injection moulding machines. The extruding step may secure a more intimate blending and thereby higher reproducibility of the final pharmaceutical product.

A pharmaceutical composition may be produced by, for example, extrusion and dip coating, injection moulding and dip coating, or by extrusion or injection moulding and solvent coating by spraying or dipping, or co-extrusion of the coating with the matrix composition and the active substance.

For further details reference is made to the experimental section herein.

The invention is further illustrated in the following figures and non-limiting examples.

FIG. 1 shows the dissolution release time as function of the content of poloxamer in two different grades of PEO, LF (lower pH) and NF in buffer 50 rpm.

FIG. 2 shows the cumulative dissolution release time as function of the content of poloxamer in PEO NF in buffer 50 rpm. Formulation 83 100% Poloxamer 188; formulation 86 comprising 60:40 PEO NF and Poloxamer, formulation 85 comprising 100% PEO NF for comparison. The dissolution analysis of the formulations showed that it is possible to control the release rate by changing the ratio of PEO to Poloxamer 188.

Figure 1:
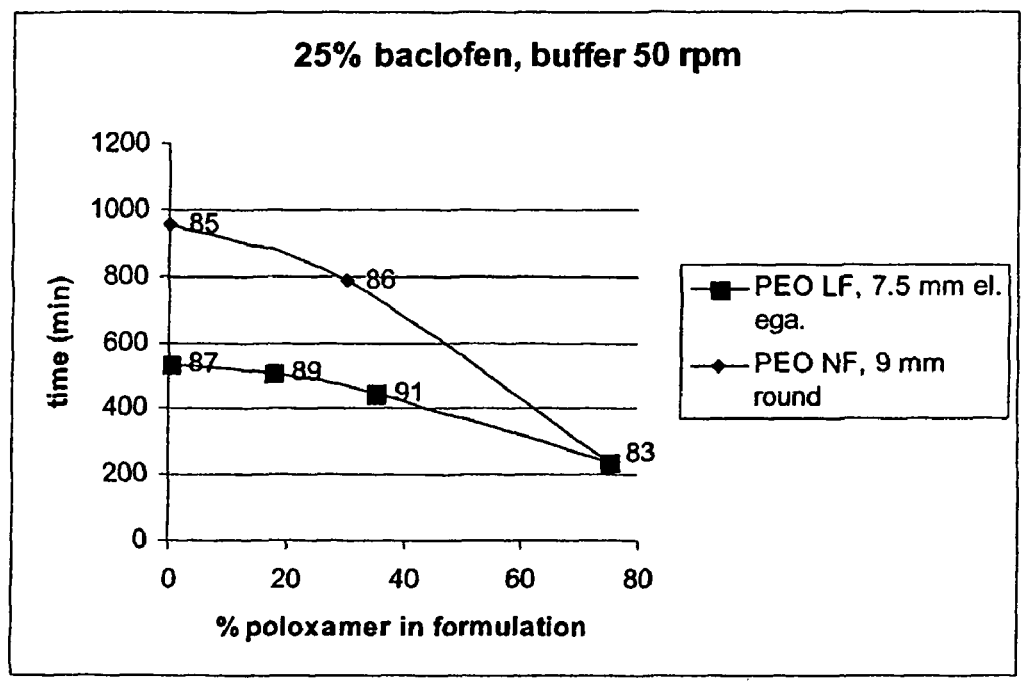
Figure 2:
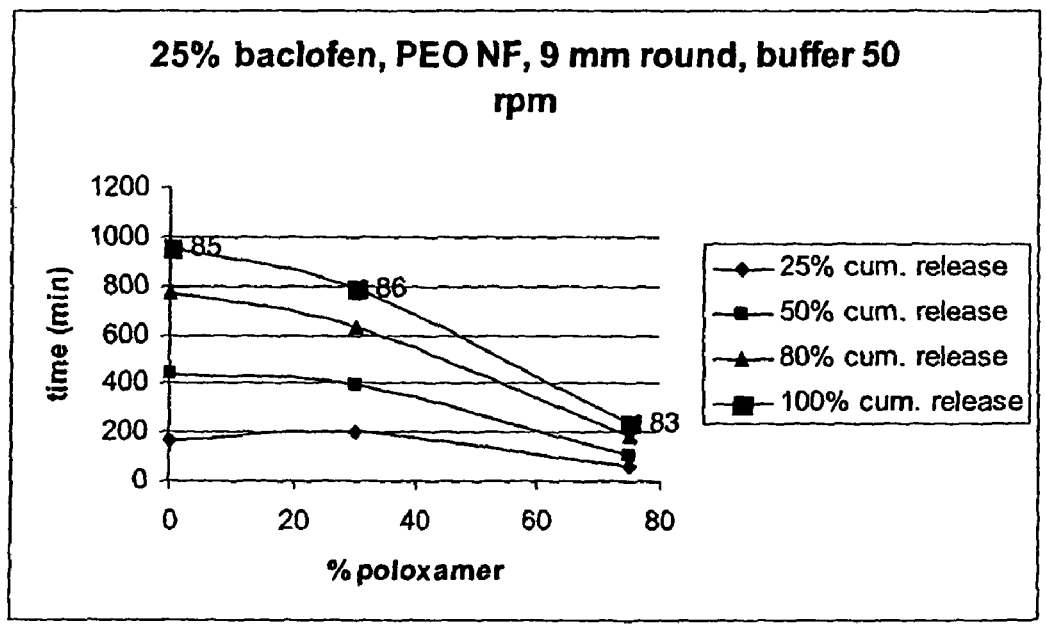
Figure 3:
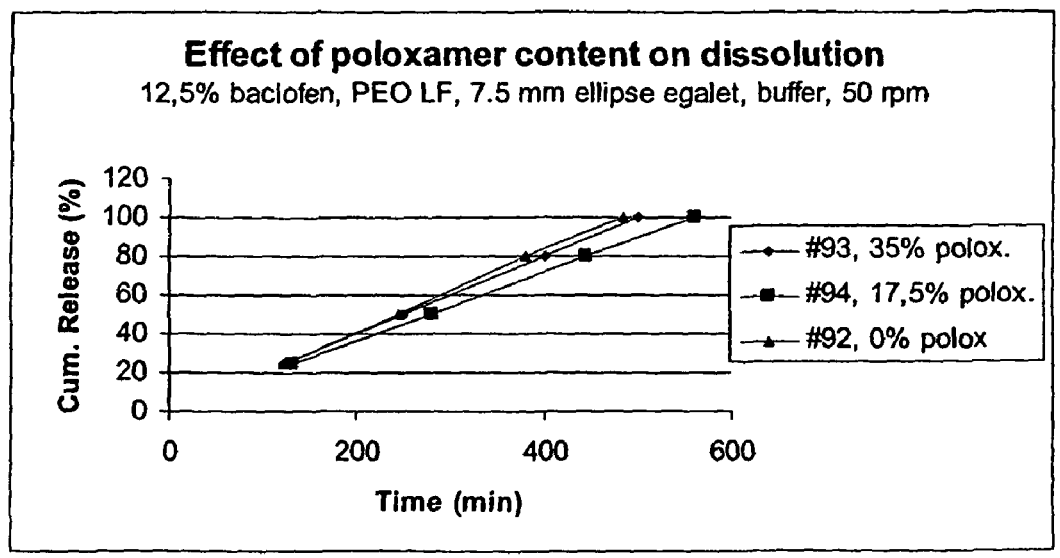
FIG. 3 shows the effect on dissolution of Poloxamer content of 12.5% of Baclofen with PEO LF.
Figure 4:
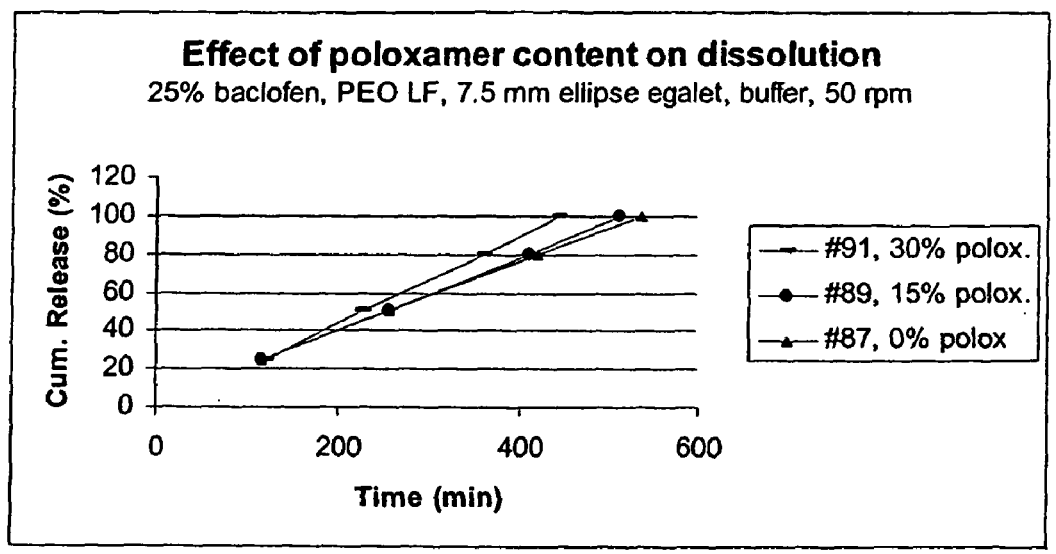
FIG. 4 shows the effect on dissolution of Poloxamer content of 25% of Baclofen with PEO LF.
Figure 5:
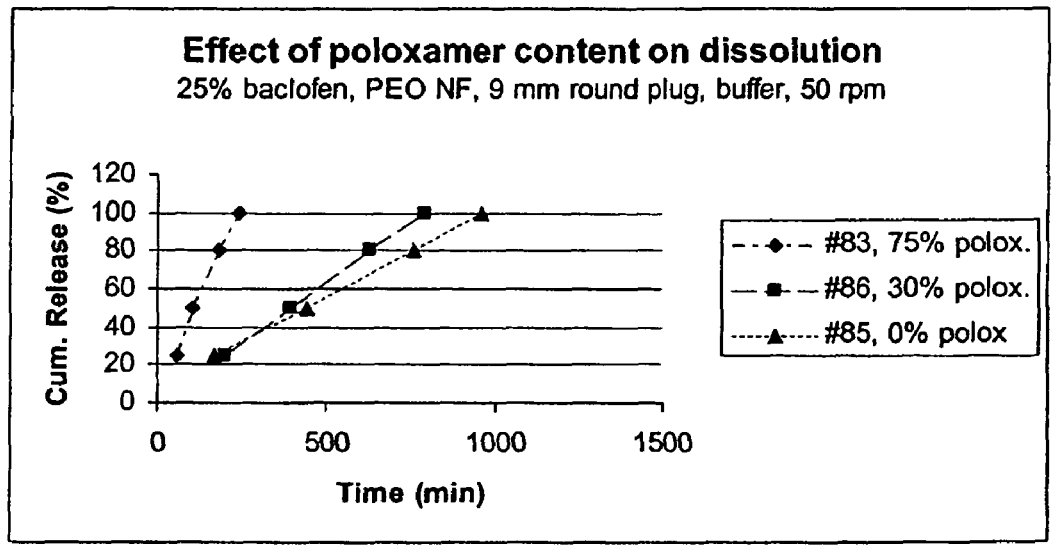
FIG. 5 shows the effect on dissolution of Poloxamer content of 25% of Baclofen with PEO NF.
Figure 6:
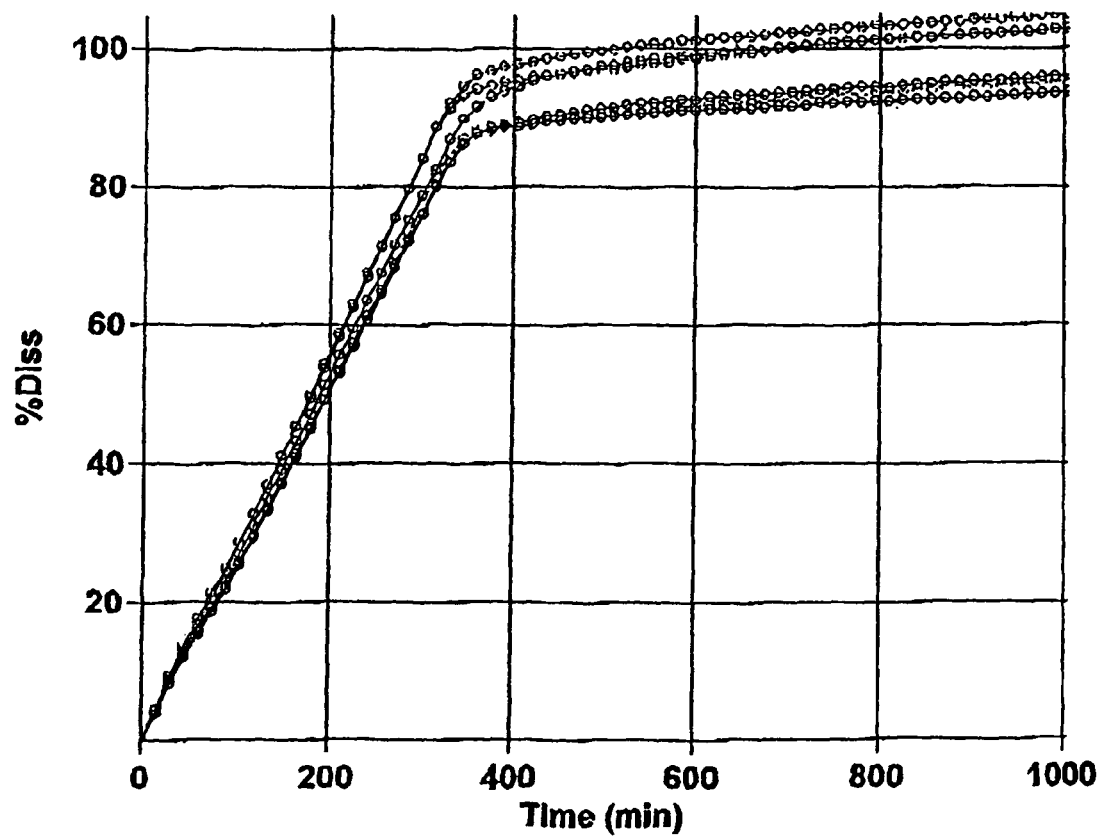

FIG. 6 shows the dissolution profile relating to a composition of Example 11 denoted 02 0143-142; the dissolution has been determined after 26 days storage at 30° C. and 60% RH. The figure shows the dissolution profile relating to a composition of denoted 02 0154-142 and demonstrated the dissolution to be unaffected by adding an extrusion step to the production.

Figure 7:
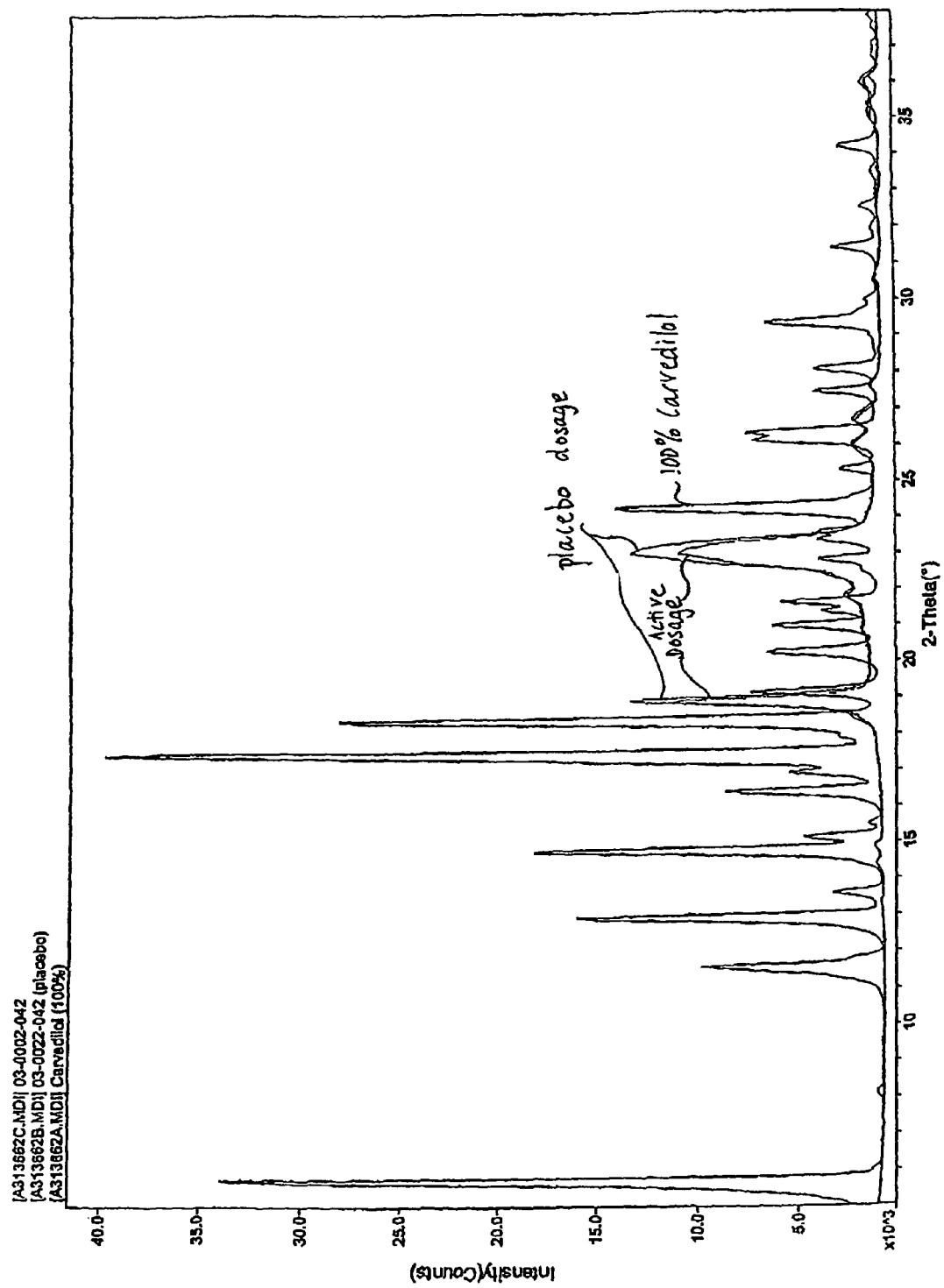

FIG. 7 shows an X-ray diffraction of the formulation denoted 03-0002-142, a similar placebo formulation wherein the carvedilol is replaced with PEO, and which has been produced under similar production parameters. The raw material carvedilol is also displayed.

Figure 8:
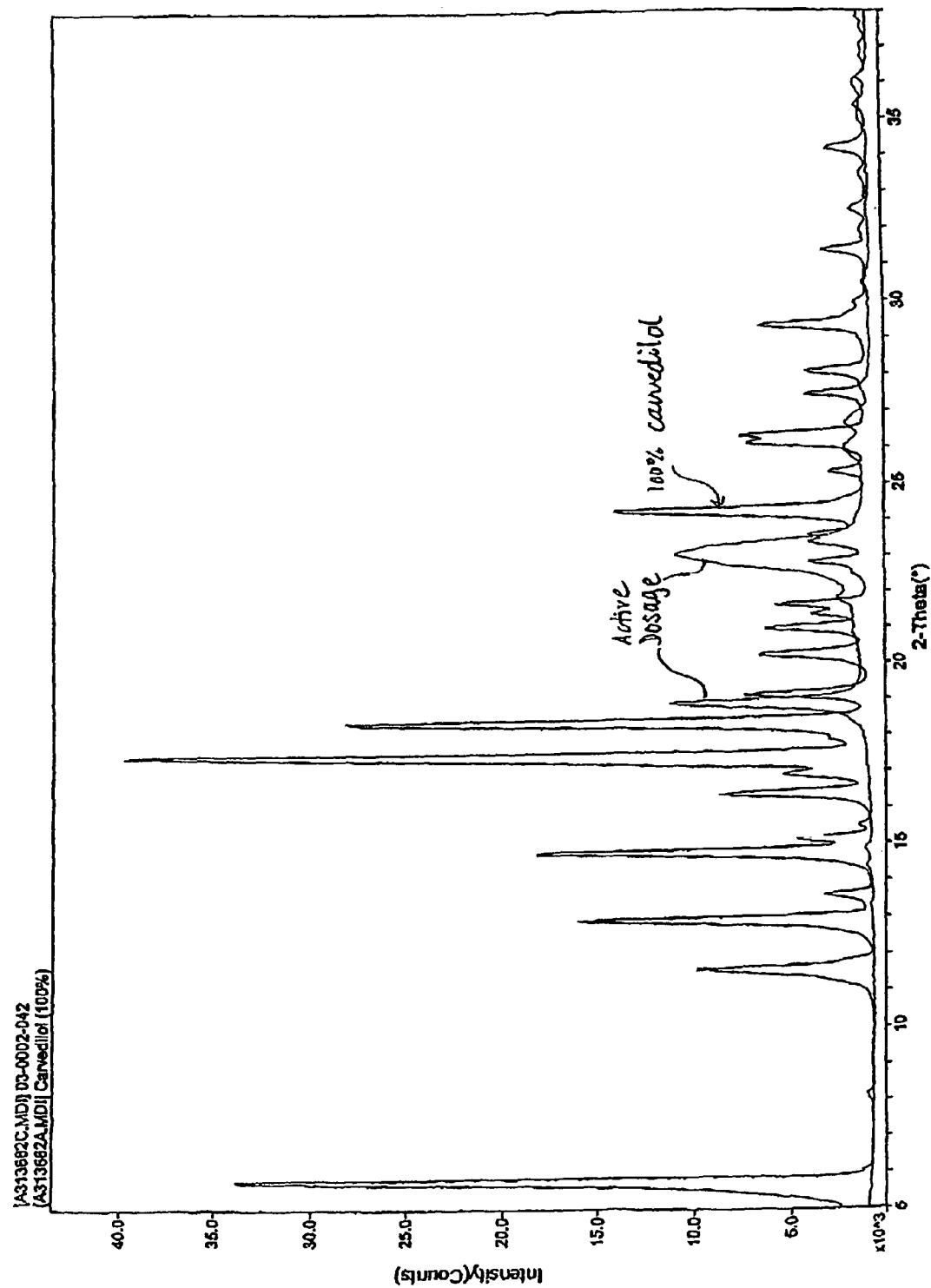

FIG. 8 shows an X-ray diffraction of the formulation denoted 03-0002-142 and the raw material carvedilol is also displayed.

Figure 9:
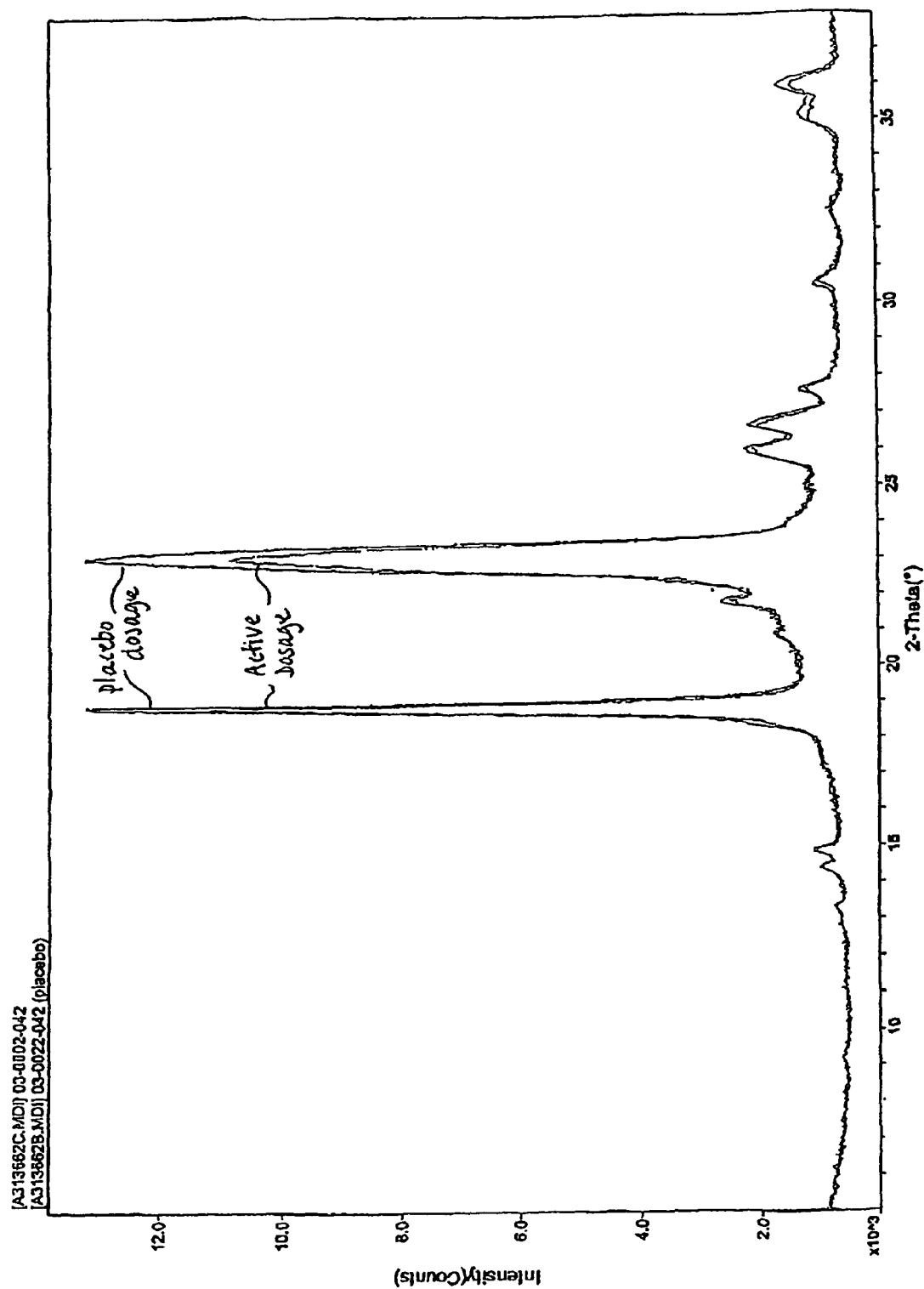

FIG. 9 shows an X-ray diffraction of the formulation denoted 03-0002-142, and the similar placebo formulation wherein the carvedilol is replaced with PEO, and which has been produced under similar production parameters. The conclusion from the x ray diffraction is that no crystalline carvedilol is present above the detection limit of 5% of the total amount of carvedilol neither in the form of the raw material or in other polymorph forms.

Figure 10:
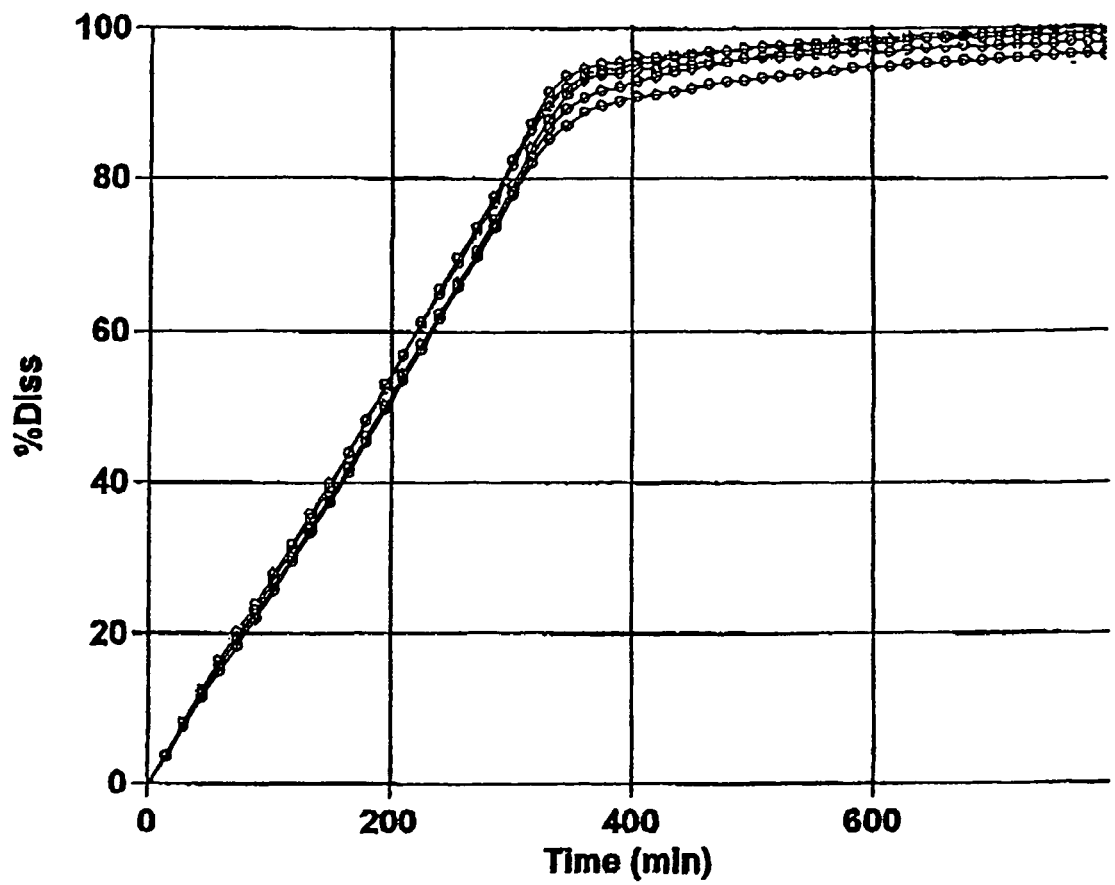

FIG. 10 shows the dissolution profile relating to a composition of Example 16 denoted 03-0002-142. The dissolution time is 274 mig (6.25 h) and the release is zero order. The dissolution media is buffer pH 6.8, rpm 50.

EXAMPLES

A general method for the preparation of a controlled release composition is described below.

Preparation of the Matrix Composition

An accurate amount of the polymer and/or polymer blend is loaded into a MTI mixer followed by an accurate amount of the active substance and of the pharmaceutically acceptable excipients(s), if any. The mixing is performed at 2050/1450 rpm and at a time period of 10 min+4 min+short final spinning. At the start of the mixing the temperature is about 19° C. (the first time period) and the final temperature of the mixture is about 52° C. (the second and third time period). The mixture is then allowed to cool to room temperature and is ready to be fed into an injection moulding machine.

Preparation of the Coating Composition

The coating composition was prepared by first adding the ethylcellulose then cetostearyl alcohol, and finally the titanium dioxide to an MTI-Mixer at a temperature about 21° C. After mixing for nearly 9 min at 1000 rpm (I: 0.9 A) the mixer was stopped (temperature about 46° C.) and the adhered material manually incorporated into the mixture. The mixture was left to cool for about 10 minutes. The mixing is then finalized with a short high-speed mix in order to minimize lumps formation. The mixture was then allowed to cool to room temperature, after which it had a suitable consistency for being fed into an injection moulding machine.

Example of Coat Composition

Batch: 58-014-01-013

| % | Batch | Material | amount (g) | Weight (g) | step |
|---|---|---|---|---|---|
| 79 | 991207-A | Ethocel | 632 | 632 | 1 |
| 20 | 990426-B | Cetylstearyl Alcohol | 160 | 160.1 | 2 |
| 1 | 97051301 | TiO$_2$ | 8 | 8.0 | 3 |
| 100 | | total | 800 | 800.1 | |

The final dosage units may be prepared according to two different methods. In one method, the coat and the matrix moulded individually followed by a manually incorporation of the moulded matrix plug into the moulded coat. The moulding machine used is an Arburg Allrounder 220 S 250/60.

In the second method, the coat and matrix are moulded in one process where the coat is moulded in a first step and the matrix is moulded directly into the coat in a second step. The moulding machine used is Arburg Allrounder 420 V 800-60/35.

The following table describes formulations having a cylindrical form and circular openings in both ends.

| Batch | Length [mm] | Diameter [mm] | Vol [mm$^3$] |
|---|---|---|---|
| 01-0034-042 | 7.5 | 5.05 | 150 |
| 01-0035-042 | 6.0 | 5.64 | 150 |
| 01-0043-042 | 9.0 | 4.6 | 150 |

The following table describes formulations having a cylindrical form and oval openings in both ends

| Batch | Length [mm] | Vol [mm$^3$] | Longest/shortest diameter [mm] | |
|---|---|---|---|---|
| 01-0075-042 | 6.0 | 150 | 8.74 | 3.64 |
| 01-0076-042 | 7.5 | 150 | 7.82 | 3.21 |

Preparation of a Coating Composition

A. Mixing in Rotolab

Accurate amounts of components are added to Rotolab mixer. Mixing is performed at 1200 rpm. Jacket on mixer is heated from 55-64° C. When product temperature is approximately 50-51° C. the mixer is stopped. Adhered materials are incorporated into mixture by manually scraping them off mixer bowl and a short spin.

B. Mixing in MTI Mixer

Accurate amounts of components are added to MTI mixer. Mixing is performed at 1000 rpm. When product temperature is approximately 46° C. the mixer is stopped. Adhered materials are incorporated into mixture by manually scraping them off mixer bowl and a short spin. The mix is left to cool for 10 minutes and then it is given a short spin to break up lumps.

Preparation of a Matrix Composition

Pre-Blends:

A pre-blend is made by hand in mortar using piston and gambling cards. Pre-blends help to get small quantities of components or non-powder components evenly distributed. The components in the pre-blend are mixed by geometric dilution. In this method the component in smallest quantity is placed in a mortar with an equal volumetric amount of another component (the diluent). The two materials are triturated (crushed and mixed) until they are well mixed. Then, an equal amount of the diluent is again added to the mixture, and trituration is repeated until they are intimately mixed. This procedure is repeated until all diluent has been added and mixed in. Either all of the pre-blend is used in a matrix composition, or a part of the stock-blend containing the desired amount of small component(s) is used.

Dryblends:

Mixing in Rotolab

Accurate amounts of components and possible pre-blends are added to Rotolab mixer. Mixing is performed at 1000 rpm for approximately 10 minutes. Jacket on mixer is not heated. Adhered materials are incorporated into mixture by manually scraping them off mixer bowl and a short spin.

Mixing in MTI Mixer

Accurate amounts of components and possible pre-blends are added to MTI mixer. Mixing is performed at 1000-1500 rpm for approximately 10 minutes. Adhered materials are incorporated into mixture by manually scraping them off mixer bowl and a short spin.

Mixing in Mortar

All components are mixed in large mortar (diameter ~30 cm) by geometric dilution. The component present in smallest quantity is added first with (some of) the component present in second smallest quantity. Then these are triturated until all of the second has been added. Then the component with third smallest quantity is added and so forth.

Wet Granulations:

Mixing in MTI Mixer

Accurate-amounts of dry components and possible pre-blends are added to MTI mixer. They are mixed for 1 minute at 1000 rpm. Then the liquid component(s) is slowly added trough a hole in the lid. This takes 4-8 minutes. Adhered materials are incorporated into mixture by manually scraping them off mixer bowl mixing for 2-4 minutes at 1000 rpm.

Combining Lots:
Gravimetric Mixing

If two or more batches are to be combined they are transferred to a container, which are manually shaken for 1-3 minutes.

Example of Compounding be Use of Extruder (Batch no.: CM79)
Batch size: 1 kg.
Equipment: 35 L/D EMP21-35 TSA co-rotating twin-screw extruder. Cooling tower with air-rings and trough. No vortex tube used. Nitrogen blanket supplied to feeder hopper.
Zone 1 (feed zone) temperature: 29-30° C.
Zone 2 (mixing zone) temperature: 60-61° C.
Zone 3 (mixing zone) temperature: 72-75° C.
Zone 4 temperature: 68-70° C.
Zone 5 temperature: 64-65° C.
Zone 6 temperature: 60-68° C.
Die Zone temperature: 61-64° C.
Torque (% of 104 amp.): 25-29%
Pressure at die: 22-25 bar
Screw speed: 56-111 rpm
Dosing unit speed: 0.4-1.0
Pellet haul off speed: 4-5
Rotor speed of pelletiser: 7

Comments: Extrudate strings were yellow in colour at first and sticky. The then turned white and less sticky.

Injection Moulding Parameters

The injection moulding setting parameters is generally within the limits disclosed below. Exact parameters are disclosed in connection to some of the individual batches for illustration.

| Barrel Temperature (° C.) | | | |
|---|---|---|---|
| Nozzle | Zone 1 | Zone 2 | Zone 3 |
| 80-100 | 75-100 | 75-100 | 65-100 |

| Hot runner temperatures Zone 0.2 (° C.) | | |
|---|---|---|
| 80-120 | | |
| Holding Pressure | Holding Time (min) | Cooling Time (Min) |
| 80-2200 | 3-50 | 3-60 |

In the following are given a number of formulation examples to illustrate the invention. The various compositions have been prepared according to the general described methods above, unless otherwise stated. Specific dissolution times are mentioned for comparison between similar matrix formulations and/or designs.

Example 1

Test on different excipients on the release time of an active ingredient with a solubility of 4.3 mg/mL, 23° C., water at pH 7.6 in a matrix composition consisting of poloxamer 188 tested in dissolution medium of pH 1.0 and buffer 6.8 in order to evaluate the effect of such excipients in a matrix composition according to the invention. The matrix composition is mixed heated and finally moulded into cylindrical plugs which are inserted into cylindrical shells before dissolution.

The release rate of baclofen from Poloxamer 188 matrix increased in buffer 6.8 when any of the organic acids were included. The most profound effect was observed when citric acid was used. This could be correlated to the different pKa-values and solubilities of the acids.

| Baclofen content: 12.5% (w/w); Poloxamer 188 as Carrier. | | |
|---|---|---|
| | Dissolution medium | Dissolution rate |
| Organic acids: | | |
| Citric acid (4.5%) | | 5 mm handmade plugs |
| ID | pH | Release (mm/min) |
| 08022004(k1_k3) | 1 | 0.083 |
| 09022004(k1_k3) | 6.8 | 0.042 |
| Citric acid (4.5%) PVP (2%) | | 5 mm handmade plugs |
| ID | pH | Release (mm/min) |
| 08022004(k4_k6) | 1 | 0.069 |
| 08022004(k4_k6) | 6.8 | 0.032 |
| Adipic acid (2.5%) | | 6 mm handmade plugs |
| ID | pH | Release (mm/min) |
| 05022004(k1_k3)C | 1 | 0.080 |
| 05022004(k4_k6)D | 6.8 | 0.032 |
| Adipic acid (5.0%) | | 6 mm handmade plugs |
| ID | pH | Release (mm/min) |
| 05022004(k1_k3)C | 1 | 0.086 |
| 05022004(k4_k6)D | 6.8 | 0.035 |
| CSA* (0.75%) + Citric Acid (15%) | | 3 mm handmade plugs |
| ID | pH | Release (mm/min) |
| 06012004(k1_k3)B | 1 | 0.056 |
| 06012004(k4_k6)B | 6.8 | 0.056 |
| CSA (0.75%) + Citric acid (15%) | | 6 mm handmade plugs |
| ID | pH | Release (mm/min) |
| 16012004(k1_k3)A | 1 | 0.055 |
| 16012004(k4_k6)A | 6.8 | 0.05 |
| TPGS (2%) + Citric acid (10%) | | 6 mm handmade plugs |
| ID | pH | Release (mm/min) |
| 18012004(k3_k4)B | 1 | 0.039 |
| 16012004(k4_k6)A | 6.8 | 0.0353 |
| TPGS (4%) + Citric acid (10%) | | 6 mm handmade plugs |
| ID | pH | Release (mm/min) |
| 16012004(k5_k6)B | 1 | 0.034 |
| 16012004(k4_k6)A | 6.8 | 0.0353 |
| Sodiumbicarbonate (10%) | | 6 mm handmade plugs |
| ID | pH | Release (mm/min) |
| 17022004(k1_k3) | 1 | 0.050 |
| not tested | 6.8 | — |
| Sodiumbicarbonate (20%) | | 6 mm handmade plugs |
| ID | pH | Release (mm/min) |
| 17022004(k4_k6) | 1 | 0.047 |
| not tested | 6.8 | — |
| Ammoniumdihydrogenphosphate (3%) | | 6 mm handmade plugs |
| ID | pH | Release (mm/min) |
| 05012004(k1_k3) | 1 | 0.057 |
| 05012004(k4_k6) | 6.8 | 0.043 |
| Ammoniumdihydrogenphosphate (6%) | | 6 mm handmade plugs |
| ID | pH | Release (mm/min) |
| 22012004(k1_k3) | 1 | 0.060 |
| Not tested | 6.8 | — |
| Surface active excipients: | | |
| Sodiumlaurylsulphate (1%) | | 6 mm handmade plugs |
| ID | pH | Release (mm/min) |
| 02022004(k3_k4) | 1 | 0.067 |
| Not tested | 6.8 | — |
| Sodiumlaurylsulphate (3%) | | 6 mm handmade plugs |
| ID | pH | Release (mm/min) |
| 02022004(k5_k6) | 1 | 0.067 |
| Not tested | 6.8 | — |
| Sodiumlaurylsulphate (5%) | | 6 mm handmade plugs |
| ID | pH | Release (mm/min) |
| 03022004(k4_k6) | 1 | 0.060 |
| Not tested | 6.8 | — |
| Lecitin (2.5%) | | 6 mm handmade plugs |
| ID | pH | Release (mm/min) |
| 11022004(k1_k2)A | 1 | 0.075 |
| 11022004(k1_k2) | 6.8 | 0.043 |
| Lecitin (5%) | | 6 mm handmade plugs |
| ID | pH | Release (mm/min) |
| 11022004(k3_k4)A | 1 | 0.063 |
| 11022004(k3_k4) | 6.8 | 0.040 |
| Lecitin (10%) | | 6 mm handmade plugs |
| ID | pH | Release (mm/min) |

-continued

Baclofen content: 12.5% (w/w); Poloxamer 188 as Carrier.

| | Dissolution medium | Dissolution rate |
|---|---|---|
| 11022004(k5_k6)A | 1 | 0.067 |
| 11022004(k5_k6) | 6.8 | 0.036 |

*(CSA = cetyl stearyl alcohol)

Example 2

Compositions with active ingredient having a solubility of 4.3 mg/mL, 23° C., water at pH 7.6 and the corresponding dissolution time and release rates in different matrix compositions according to the invention. The results demonstrated the possibility of controlling the release rate by use of different ratios of the PEO and block copolymer according to the invention.

| Batch No. | API Excipients | Appearance | Dissolution Condition | 25% | 50% | 80% | 100% | Release rate (min/mm) |
|---|---|---|---|---|---|---|---|---|
| 03-0083-105 | 25% W/W 75% w/w Poloxamer 188 | 9 mm round plug | Buffer pH 6.8 50 rpm | 60 | 105 | 180 | 240 | 27 |
| 03-0085-105 | 25% W/W 75% w/w PEO 200.000 NF | 9 mm round plug | Buffer pH 6.8 50 rpm | 170 | 440 | 755 | 955 | 106 |
| 03-0086-105 | 25% W/W 45% w/w PEO 200.000 NF 30% w/w Poloxamer 188 (60:40) | 9 mm round plug | Buffer pH 6.8 50 rpm | 198 | 395 | 630 | 786 | 87 |
| 03-0087-105 | 75% w/w PEO 200.000 LF | 7.5 mm ellipse Egalet | Buffer pH 6.8 50 rpm | 115 | 255 | 420 | 535 | 71 |
| 03-0089-105 | 25% W/W 60% w/w PEO 200.000 LF 15% w/w Poloxamer 188 (80:20) | 7.5 mm ellipse Egalet | | | | | | |
| 03-0091-105 | 25% W/W 45% w/w PEO 200.000 LF 30% w/w Poloxamer 188 (60:40) | 7.5 mm ellipse Egalet | Buffer pH 6.8 50 rpm | 120 | 225 | 360 | 445 | 59 |
| 03-0093-105 | 12.5% W/W 52.5% w/w PEO 200.000 LF 35% w/w Poloxamer 188 (60:40) | 7.5 mm ellipse Egalet | Buffer pH 6.8 50 rpm | 120 | 250 | 400 | 500 | 67 |
| | | | 0.1N HCl 50 rpm | 75 | 165 | 255 | 330 | 44 |
| | | | 0.01N HCl 50 rpm | 75 | 165 | 260 | 335 | 45 |
| 03-0094-105 | 12.5% W/W 70% w/w PEO 200.000 LF 17.5% w/w Poloxamer 188 (80:20) | 7.5 mm ellipse Egalet | Buffer pH 6.8 50 rpm | 130 | 280 | 445 | 560 | 75 |
| | | | 0.01 N HCl 50 rpm | 95 | 185 | 290 | 365 | 49 |
| 03-0097-105 | 25% W/W 45% w/w PEO 200.000 LF 30% w/w Poloxamer 188 | 3 × 3 mm plugs (9 mm in total) | Buffer pH 6.8 50 rpm | | | | | |
| | | | 0.01 N HCl 50 rpm | 75 | 185 | 290 | 315 | 35 |

-continued

| Batch No. | API | Excipients | Appearance | Dissolution Condition | 25% | 50% | 80% | 100% | Release rate (min/mm) |
|---|---|---|---|---|---|---|---|---|---|
| 03-0101-105 | 12.5% W/W | 70% w/w PEO 200.000 NF 17.5% w/w Poloxamer 188 (80:20) | 7.5 mm ellipse Egalet | Buffer pH 6.8 50 rpm | 135 | 265 | 435 | 540 | 72 |
| | | | | 0.1 N HCl 50 rpm | 95 | 185 | 290 | 365 | 49 |

Dissolution parameters for Baclofen formulations according to the invention are disclosed in FIG. 1 to FIG. 5.

From the above Examples with Baclofen 25% it can be seen that the ratio between the dissolution rate for PEO NF and Polxamer 188 as the sole polymer is 106/27 corresponding to a factor 3,93. By use of a 60:40 blend, the delease rate is increased compared to PEO NF alone to a factor of 1.22. In other words, the release rate is reduced by approximately a factor 3 from the rate obtained with PEO alone by substituting the polymer carrier PEO NF with 40% of the Poloxamer.

It is clear that suitable desired release times can be found from a graph based on a small number of tests.

Example 3

A composition (batch No. 02-0121-042) according to the invention was prepared from the following ingredients.

| Matrix: | % w/w |
|---|---|
| PEC 200.000 LF | 70.68% |
| PolyXamer [Lutrol F127] | 16.97% |
| Carvedilol | 11.67% |
| PM | 0.19% |
| BHT | 0.49% |

One doses form contains 22 mg Carvedilol. The composition was 6 mm long and had an oval cross sectional shape.

Example 4

A composition (batch No. 02-0128-042) according to the invention was prepared from the following ingredients.

| Matrix: | % w/w |
|---|---|
| PEO 200.000 (LF) | 74.30% |
| PoloXamer (Lutrol F68) | 13% |
| Carvedilol | 12.0% |
| Sodium Metabisulfite | 0.2% |
| BHT | 0.5% |

One doses form contains 23 mg carvedilol. The composition was 9 mm long and had a round cross sectional shape.

Example 5

A composition (batch No. 02-0130-042) according to the invention was prepared from the following ingredients.

| Matrix: | % w/w |
|---|---|
| PEO 200.000 LF | 64.80% |
| PoloXamer [Lutrol F68] | 20.5% |
| Carvedilol | 14.0% |
| PM | 0.2% |
| BHT | 0.5% |

One doses form contains 26 mg carvedilol. The composition was 6 mm long and had an oval cross sectional shape.

The dissolution showed zero order release and a dissolution time at 330 min (5.5 h)

Example 6

A composition (batch No. 02-0131-042) according to the invention was prepared from the following ingredients.

| Matrix: | % w/w |
|---|---|
| PEO 200.000 (LF) | 69.85% |
| PoloXamer (Lutrol F68) | 17.45 |
| Carvedilol | 12.0% |
| Sodium Metabisulfite | 0.2% |
| BHT | 0.5% |

One doses form contains 23 mg carvedilol. The composition was 9 mm long and had a round cross sectional shape.

Example 7

A composition (batch No. 02-0132-042) according to the invention was prepared from the following ingredients.

| Matrix: | % w/w |
|---|---|
| PEO 200.000 (LF) | 65.45% |
| PoloXamer (Lutrol F68) | 21.85% |
| Carvedilol | 12.0% |
| Sodium Metabisulfite | 0.2% |
| BHT | 0.5% |

The composition was 9 mm long and had a round cross sectional shape.

Example 8

A composition (batch No.: 02-0133-042) according to the invention was prepared from the following ingredients.

| Matrix: | % w/w |
|---|---|
| PEO 200.000 (LF) | 61.10% |
| PoloXamer (Lutrol F68) | 26.2% |
| Carvedilol | 12.0% |
| Sodium Metabisulfite | 0.2% |
| BHT | 0.5% |

One doses form contains 22 mg carvedilol. The composition was 9 mm long and had a round cross sectional shape.

Example 9

A composition (batch No. 02-0134-042) according to the invention was prepared from the following ingredients.

| Matrix: | % w/w |
|---|---|
| PEO 200.000 LF | 61.40% |
| PoloXamer [Lutrol F68] | 19.4% |
| Carvedilol | 14.0% |
| PM | 0.2% |
| BHT | 0.5% |
| Ortho-Phosphoric Acid | 4.5% |

One doses form contains 25 mg carvedilol. The composition was 6 mm long and had an oval cross sectional shape.

A similar formulation (Batch 02-0140-042) with same volume and 7.5 mm oval shape was prepared.

Dissolution showed zero order for both and a dissolution time of:

370 min for the 7.5 mm corresponding to an erosion rate of 1.22 mm/h.

290 min for the 6 mm corresponding to an erosion rate of 1.24 mm/h.

Example 10

A composition (batch No.: 02-0141-042) according to the invention was prepared from the following ingredients.

| Matrix: | % w/w |
|---|---|
| PEO 200.000 LF | 60.78% |
| PoloXamer [Lutrol F68] | 19.21% |
| Carvedilol | 13.86% |
| PM | 0.20% |
| BHT | 0.50% |
| Ortho-Phosphoric Acid | 4.45% |
| TiO$_2$ | 1.00% |

One doses form contains 25 mg carvedilol. The composition was 7.5 mm long and had an oval cross sectional shape. Dissolution did not show any significant change by addition of TiO$_2$ when compared to the dissolution of a similar batch (02-0140-042, matrix identical with batch 0134).

Example 11

A composition (batch No. 02-0143-042) according to the invention was prepared from the following ingredients.

| Matrix: | % w/w |
|---|---|
| PEO 200.000 LF | 60.60% |
| PoloXamer [Lutrol F68] | 19.2% |
| Carvedilol | 14.0% |
| PM | 0.2% |
| BHT | 0.5% |
| Ortho-Phosphoric Acid | 4.5% |
| KH$_2$PO$_4$ | 1.0% |

One doses form contains 25 mg carvedilol. The composition was 7.5 mm long and had an oval cross sectional shape.

Dissolution: As seen from FIG. 11 (the lover curve presenting vessel 4, 5, and 6) the dissolution is zero order. Dissolution time from raw data 360 min (6 h).

Example 12

A composition (batch No. 02-0145-042) for comparison was prepared from the following ingredients.

| Matrix: | % w/w |
|---|---|
| PEO 200.000 LF | 79.80% |
| Carvedilol | 14.0% |
| PM | 0.2% |
| BHT | 0.5% |
| Ortho-Phosphoric Acid | 4.5% |
| KH$_2$PO$_4$ | 1.0% |

The composition was 7.5 mm long and had an oval cross sectional shape.

Example 13

A composition (batch No. 02-0151-042) according to the invention was prepared from the following ingredients.

| Matrix: | % w/w |
|---|---|
| PEO 200.000 LF | 61.40% |
| PoloXamer [Lutrol F68] | 19.4% |
| Carvedilol | 14.0% |
| PM | 0.2% |
| BHT | 0.5% |
| Ortho-Phosphoric Acid | 4.5% |

One doses form contains 25 mg carvedilol. The composition was 7.5 mm long and had an oval cross sectional shape.

Example 14

A composition (batch No. 02-0152-042) according to the invention was prepared from the following ingredients.

| Matrix: | % w/w |
|---|---|
| PEO 200.000 LF | 60.60% |
| PoloXamer [Lutrol F68] | 19.2% |
| Carvedilol | 14.0% |
| PM | 0.2% |
| BHT | 0.5% |
| Ortho-Phosphoric Acid | 4.5% |
| KH$_2$PO$_4$ | 1.0% |

One doses form contains 25 mg carvedilol. The composition was 7.5 mm long and had an oval cross sectional shape.

Example 15

A composition (batch No. 02-0154-042) according to the invention was prepared from the following ingredients.

| Matrix: | % w/w |
|---|---|
| PEO 200.000 LF | 61.40% |
| PoloXamer [Lutrol F68] | 19.4% |
| Carvedilol | 14.0% |
| PM | 0.2% |
| BHT | 0.5% |
| Ortho-Phosphoric Acid | 4.5% |

One doses form contains 25 mg carvedilol. The composition was 7.5 mm long and had an oval cross sectional shape.

Dissolution: As seen from FIG. 11 (the upper curve presenting vessel 1, 2, and 3) the dissolution is zero order. Dissolution time from raw data 360 min (6 h). Accordingly, the dissolution time is not altered by extrusion compounding as the composition corresponds to batch 0143 of Example 34.

Example 16

A composition (batch No. 03-0002-042) according to the invention was prepared from the following ingredients.

| Matrix: | % w/w |
|---|---|
| PEO 200.000 LF | 60.6% |
| PoloXamer [Lutrol F68] | 19.2% |
| Carvedilol | 14% |
| Potassium Metabisulfite | 0.2% |
| BHT | 0.5% |
| Ortho-Phosphoric Acid | 4.5% |
| $KH_2PO_4$ | 1.0% |

One doses form contains 25 mg carvedilol. The composition was 7.5 mm long and had an oval cross sectional shape.

The invention claimed is:

1. A controlled release pharmaceutical composition for oral use in the form of a coated matrix composition, the matrix composition comprising
i) a mixture of a first polymer and a second polymer that have plasticizing properties and which have melting points or melting intervals of a temperature of at the most 200° C.,
the first polymer being selected from the group consisting of polyethylene glycols and polyethylene oxides having a molecular weight of at least about 20,000 in crystalline and/or amorphous form, or a mixture such polymers, and
the second polymer being selected from poloxamers having an HLB value of at least 18,
ii) a therapeutically, prophylactically and/or diagnostically active substance, wherein the concentration of the second polymer in the matrix composition is from about 5 to about 90% w/w,
the matrix composition being provided with a coating having at least one opening exposing at least one surface of said matrix, the coating comprising
a first cellulose derivative which has thermoplastic properties and which is substantially insoluble in the aqueous medium in which the composition is to be used,
and at least one of:
a second cellulose derivative which is soluble or dispersible in water,
a plasticizer, and
a filler,
wherein the active substance is released with a substantially zero order release.

2. A composition according to claim 1, wherein the polyethylene oxide has a molecular weight selected from the group consisting of about 35,000 daltons, about 50,000 daltons, about 100,000 daltons, and about 200,000 daltons.

3. A composition according to claim 1, wherein the first polymer has a melting point of about 20-120° C.

4. A composition according to claim 1, wherein the concentration of the first polymer in the matrix composition is from about 10 to about 95%.

5. A composition according to claim 1, wherein the second polymer has a molecular weight of at least about 2,000 daltons.

6. A composition according to claim 1, wherein the second polymer is a poloxamer that has the formula $HO(C_2H_4O)_a(C_3H_6O)_b(C_2H_4O)_aH$, and a is an integer from about 10 to about 150.

7. A composition according to claim 6, wherein the poloxamer has a molecular weight of from about 2,000 daltons to about 20,000 daltons.

8. A composition according to claim 1, wherein the second polymer has a melting point of about 20-120° C.

9. A composition according to claim 1, wherein the second polymer has an HLB value of at least about 20.

10. A composition according to claim 1, wherein the concentration of the second polymer in the matrix composition is from about 10% to about 80% w/w.

11. A pharmaceutical composition according to claim 1 that provides controlled release of the active substance into an aqueous medium by erosion of at least one surface of the composition.

12. A composition according to claim 1, wherein the active substance is present in any of its crystalline, polymorphous or amorphous forms or mixtures thereof.

13. A pharmaceutical composition according to claim 1, wherein the active substance at least partially is present in solid form in the dispersion.

14. A pharmaceutical composition according to claim 1, wherein the active substance at least partially is present in a molecular dispersion.

15. A pharmaceutical composition according to claim 14, wherein the active substance is present in a molecular dispersion including a solid solution.

16. A pharmaceutical composition according to claim 15, wherein the active substance at least partially is present in a colloidal dispersion.

17. A pharmaceutical composition according to claim 12, wherein the active substance at least partially is present in a crystalline form.

18. A pharmaceutical composition according to claim 1, wherein the active substance at least partially is present in amorphous form with a mean particle size of from about 0.01 μm to about 500 μm.

19. A composition according to claim 1, wherein the first and the second polymer together form a dispersion medium in which the active substance is contained.

20. A composition according to claim 1 comprising a stabilizing agent.

21. A composition according to claim 20, wherein the stabilizing agent is selected from the group consisting of diffusion and dissolution adjusting agents, pH-adjusting agents, buffering agents, agents that does not increase the mobility of the ingredients in the composition, agents that prevent crystal formation and agents that have antioxidative properties.

22. A composition according to claim 20, wherein the stabilizing agent is selected from the group consisting of inorganic acids, inorganic bases, inorganic salts, organic acids or bases and pharmaceutically acceptable salts thereof, saccharides, oligosaccharides, polysaccharides, and cellulose and cellulose derivatives, or mixtures thereof.

23. A composition according to claim 22, wherein the organic acid is selected from the group consisting of acetic acid, ethanoic acid, succinic acid, citric acid, tartaric acid, acrylic acid, benzoic acid, malic acid, maleic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, pyruvic acid, aspartic and glutamic acid, or mixtures thereof.

24. A composition according to claim 22, wherein the inorganic acid is pyrophosphoric acid, glycerophosphoric acid, phosphoric acid, boric acid, hydrochloric acid, or sulfuric acid, or mixtures thereof.

25. A composition according to claim 22, wherein the suitable inorganic compounds include aluminium.

26. A composition according to claim 22, wherein the suitable organic bases are selected from the group consisting of p-nitrophenol, succinimide, benzenesulfonamide, 2-hydroxy-2cyclohexenone, imidazole, pyrrole, diethanolamine, ethyleneamine, tris (hydroxymethyl) aminomethane, hydroxylamine and derivates of amines, sodium citrate, aniline, and hydrazine, or mixtures thereof.

27. A composition according to claim 22, wherein the suitable inorganic bases are selected from the group consisting of aluminium oxides, sodium hydroxide, potassium hydroxide, calcium carbonate, ammonium carbonate, ammnonium hydroxide, KOH and mixtures thereof.

28. A composition according to claim 22, wherein the pharmaceutically acceptable salt of an organic acid is selected from the group consisting of sodium phosphate, sodium dihydrogenphosphate, disodium hydrogenphosphate, potassium phosphate, potassium dihydrogenphosphate, potassium hydrogenphosphate, calcium phosphate, dicalcium phosphate, sodium sulfate, potassium sulfate, calcium sulfate, sodium carbonate, sodium hydrogencarbonate, potassium carbonate, potassium hydrogencarbonate, calcium carbonate, magnesium carbonate, sodium acetate, potassium acetate, calcium acetate, sodium succinate, potassium succinate, calcium succinate, sodium citrate, potassium citrate, calcium citrate, sodium tartrate, potassium tartrate, calcium tartrate, zinc gluconate, zinc sulphate and mixtures thereof.

29. A composition according to claim 22, wherein the inorganic salt is selected from the group consisting of sodium chloride, potassium chloride, calcium chloride, magnesium chloride and mixtures thereof.

30. A composition according to claim 22, wherein the pharmaceutically acceptable excipient is selected from glucose, ribose, arabinose, xylose, lyxose, allose, altrose, inosito, glucose, sorbitol, mannose, gulose, idose, galactose, talose, mannitol, fructose, lactose, sucrose, dextrin, dextran, amylose, xylan, cellulose and cellulose derivatives, amylopectin, pectin, starch, sodium starch, kaolin, bentonit, acacia, alginic acid, sodium alginate, calcium alginate, gelatin, dextrose, molasses, extract of Irish moss, panwar gum, ghatti gum, mucilage of isapol husk, veegum, glycollate, magnesium stearate, calcium stearate, stearic acid, talc, titanium dioxide, silicium dioxide, clays, croscarmellose, gums, agar, and mixtures thereof.

31. A composition according to claim 1 further comprising a pharmaceutically acceptable excipient selected from the group consisting of fillers, diluents, disintegrants, glidants, pH-adjusting agents, viscosity adjusting agents, solubility increasing or decreasing agents, osmotically active agents and solvents.

32. A composition according to claim 22, wherein the stabilizing agent is citric acid including solvates and anhydrates thereof.

33. A composition according to claim 32, wherein the citric acid has a water content of at the most about 15% w/w.

34. A composition according to claim 22, wherein the stabilizing agent is a phosphoric acid or a phosphonic acid or a salt thereof.

35. A composition according to claim 34, wherein the phosphoric acid is ortho or meta phoshoric acid or a mixture thereof.

36. A composition according to claim 1, wherein the concentration of the active substance in the composition corresponds to a concentration of at the most the saturated concentration in component i) at a temperature corresponding to the melting point or the lowest end point of the melting interval of component i).

37. A composition according to claim 1, wherein the first polymer is of a quality that ensures that free radicals formed, if any, do not significantly increase the degradation of the active substance in the composition.

38. A composition according to claim 1 further comprising one or more antioxidants that inhibits the formation of peroxides and/or inactivates any peroxides present.

39. A composition according to claim 1, wherein the active substance has antioxidant properties.

40. A composition according to claim 1, wherein the composition is stable with respect to physical stability.

41. A composition according to claim 1, wherein the composition is stable with respect to in vitro dissolution of the active substance from the composition.

42. A composition according to claim 41, wherein the composition is stable with respect to in vitro dissolution behaviour in such a manner that $t_{50\%}$, (the time for 50% w/w of the active substance to dissolve in a dissolution medium), differs at the most ±20% w/w when two compositions from the same batch are compared with a time difference of 2 weeks under similar storage and test conditions.

43. A composition according to claim 1, wherein the composition is stable with respect to chemical stability of the active substance.

44. A composition according to claim 43, wherein the concentration of the active substance in the composition decreases at the most 20% w/w when stored at room temperature for a time period of at least 3 months and a relative humidity of at the most 75%.

45. A composition according to claim 1, wherein the active substance is present in the composition in a concentration of from about 0.1 to about 98% w/w.

46. A composition according to claim 1, wherein the active substance has a solubility of at the most about 3 mg/ml in water at ambient temperature.

47. A composition according to claim 1, wherein in the aqueous medium in which the composition is to be used, the coating does not completely crumble or erode before the matrix has completely eroded.

48. A composition according to claim 1, wherein said first cellulose derivative is a cellulose ether which, when heated, is shapeable by molding or extrusion.

49. A composition according to claim 48 in which the cellulose ether comprises at least one ethylcellulose.

50. A composition according to claim 1 in which said first cellulose derivative is selected from the group consisting of cellulose acetate, cellulose propionate and cellulose nitrate.

51. A composition according to claim 1 in which said second cellulose derivative is selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellylose, hydroxyethylmethylcellulose, hydroxypropylcellulose, hydroxymethylcellulose and hydroxymethylpropylcellulose.

52. A composition according to claim 51 in which said salt of carboxymethylcellulose is selected from the group consisting of alkali metal and alkaline earth metal salts.

53. A composition according to claim 1, in which said plasticizer is selected from the group consisting of phosphate esters; phthalate esters; amides; mineral oils;
  fatty acids and esters thereof with polyethylene glycol, glycerin or sugars; fatty alcohols and ethers thereof with polyethylene glycol, glycerin or sugars; vegetable oils and hydrogenated vegetable oils; nitrobenzene, carbon disulfide, β-naphtyl salicylate, phthalyl glycolate, and diocyl phthalate.

54. A composition according to claim 53 in which said fatty alcohol is selected from the group consisting of cetostearyl alcohol, cetyl alcohol, stearyl alcohol, oleyl alcohol and myristyl alcohol.

55. A composition according to claim 1 in which said plasticizer is a non-ionic surfactant.

56. A composition according to claim 1, wherein the solid dispersion does not contain polyethylene glycol 2000 monostearate or polyethylene glycol 400 monostearate.

57. A composition according to claim 1, wherein the first polymer has a molecular weight of at least 100,000 daltons and at the most 400,000 daltons.

58. A composition according to claim 1, wherein release of the active substance from the composition is zero order and about 50% w/w of the active substance is released from the composition within 5-6 hours from start of release as measured by an in vitro dissolution test (USP) at 50 RPM in 0.1N HCl (pH 1) or in buffer (pH 6.8).

59. A composition according to claim 1, wherein release of the active substance from the composition is zero order and about 50% w/w of the active substance is released from the composition within 4-5 hours from start of release as measured by an in vitro dissolution test (USP) at 50 RPM in 0.1N HCl (pH 1) or in buffer (pH 6.8).

60. A composition according to claim 1, wherein release of the active substance from the composition is zero order and about 50% w/w of the active substance is released from the composition within 3-4 hours from start of release as measured by an in vitro dissolution test (USP) at 50 RPM in 0.1N HCl (pH 1) or in buffer (pH 6.8).

61. A composition according to claim 1, wherein release of the active substance from the composition is zero order and about 50% w/w of the active substance is released from the composition within 2-3 hours from start of release as measured by an in vitro dissolution test (USP) at 50 RPM in 0.1N HCl (pH 1) or in buffer (pH 6.8).

62. A composition according to claim 1, wherein release of the active substance from the composition is substantially delayed for 0.25 to 4 hours before the zero order release starts as measured by an in vitro dissolution test (USP) at 50 RPM in 0.1N HCl (pH 1) or in buffer (pH 6.8).

63. A method for preparing a composition according to claim 1, comprising injection moulding of a melted or semi-solid mixture of the matrix composition components into a suitable form, application of the coating by injection moulding, and cooling the thus prepared coated composition to solidify the composition.

64. A method according to claim 63, wherein the method is a substantially single continuous process.

65. A method according to claim 64, wherein the cooling is performed under controlled conditions to a temperature of from about 0° C. to about 20° C.

66. A method according to claim 1 comprising a step of heating while the polymer and the active substance is in physical contact with each other.

67. A composition according to claim 1, wherein the polyethylene glycol and/or polyethylene oxide has a molecular weight of from about 20,000 to about 700,000 daltons.

68. A composition according to claim 4, wherein the concentration of the first polymer in the matrix composition is from about 20 to about 95%.

69. A composition according to claim 7, wherein the poloxamer has a molecular weight of from about 4,000 daltons to about 15,000 daltons.

70. A controlled release pharmaceutical composition for oral use in the form of a coated matrix composition, the matrix composition comprising
  (i) a mixture of a first polymer and a second polymer that have plasticizing properties and which have melting points or melting intervals of a temperature of at the most 200° C.,
    the first polymer being selected from the group consisting of polyethylene glycols and polyethylene oxides having a molecular weight of at least about 20,000 daltons in crystalline and/or amorphous form, or a mixture of such polymers, and
    the second polymer being selected from block copolymers of ethylene oxide and propylene oxide having an HLB value of at least 18, and
  (ii) a therapeutically, prophylactically and/or diagnostically active substance,
  wherein the concentration of the second polymer in the matrix composition is from about 5 to about 90% w/w,
  the matrix composition being provided with a coating which is substantially insoluble in and impermeable to body fluids during the intended release periods, the coating having at least one opening exposing one surface of said matrix,
  the coating comprising one or more coating polymers which can be processed by extrusion, solution, or in the form of a dispersion, the one or more coating polymers being selected from the group consisting of cellulose acetate, polyamide, polyethylene, polyethylene terephthalate, polypropylene, polyurethane, polyvinyl acetate, polyvinyl chloride, silicone rubber, latex, polyhydroxybutyrate, polyhydroxyvalerate, teflon, polylactic acid or polyglycolic acid and copolymers thereof, ethylene vinyl acetate (EVA) copolymers, styrene-butadienestyrene (SBS) copolymers and styrene-isoprene-styrene (SIS) copolymers.

71. The composition according to claim 70, wherein the polyethylene glycol and/or polyethylene oxide has a molecular weight selected from the group consisting of from about 20,000 to about 700,000 daltons, from about 20,000 to about 600,000 daltons, from about 35,000 to about 500,000 daltons, from about 35,000 to about 400,000 daltons, from about 35,000 to about 300,000 daltons, from about 50,000 to about 300,000 daltons, about 35,000 daltons, about 50,000 daltons, about 75,000 daltons, about 100,000 daltons, about 150,000 daltons, about 200,000 daltons, about 250,000 daltons, about 300,000 daltons and about 400,000 daltons.

72. The composition according to claim 70, wherein the concentration of the first polymer in the matrix composition is selected from the group consisting of from about 10 to about 99.5% w/w, from about 20 to about 99% w/w, from about 30 to about 99% w/w, from about 35 to about 95% w/w, from about 35 to about 90% w/w, from about 35 to about 85% w/w, from about 35 to about 80% w/w, from about 40 to about 75% w/w, from about 45 to about 70% w/w, from about 45 to about 65% w/w, from about 55 to about 85% w/w and from about 60 to about 85% w/w.

73. The composition according to claim 70, wherein the second polymer has a molecular weight of at least about 2,000 daltons.

74. The composition according to claim 70, wherein the second polymer is a poloxamer having a molecular weight selected from the group consisting of from about 2,000 daltons to about 20,000 daltons, from about 4,000 daltons to about 15,000 daltons and from about 6,000 daltons to about 10,000 daltons.

75. The composition according to claim 70, wherein the second polymer has a melting point selected from the group consisting of from about 20-120° C., from about 30-100° C. and from about 40-80° C.

76. The composition according to claim 70, wherein the second polymer has an HLB value of at least about 20.

77. The composition according to claim 70, wherein the concentration of the second polymer in the matrix composition is selected from the group consisting of from about 10% to about 90% w/w, from about 10% to about 80% w/w, from about 10% to about 70% w/w, from about 10% to about 60%, from about 10% to about 50%, from about 15% to about 50% w/w, from about 10% to about 45% w/w, from about 10% to about 40% w/w, from about 15% to about 40% w/w, from about 15% to about 35% w/w and from about 15% to about 30% w/w.

78. The pharmaceutical composition according to claim 70, wherein said composition provides controlled release of the active substance into an aqueous medium by erosion of at least one surface of the composition.

79. The composition according to claim 70, wherein the active substance is present in any of its crystalline, polymorphous or amorphous forms or mixtures thereof.

80. A pharmaceutical composition according to claim 70, wherein the active substance at least partially is present in a molecular dispersion.

81. The composition according to claim 70, further comprising a stabilizing agent.

82. The composition according to claim 81, wherein the stabilizing agent is selected from the group consisting of inorganic acids, inorganic bases, inorganic salts, organic acids or bases and pharmaceutically acceptable salts thereof, saccharides, oligosaccharides, polysaccharides, cellulose derivatives, and mixtures thereof.

83. The composition according to claim 70, wherein the block copolymer of ethylene oxide and propylene oxide is selected from the group consisting of poly(ethylene-glycol-b-(DL-lactic acid-co-glycolic acid)-b-ethylene glycol (PEG-PLGA PEG), poly((DL-lactic acid-co-glycolic acid)-g-ethylene glycol) (PLGA-g-PEG), poloxamers and polyethylene oxide-polypropylene oxide (PEO-PPO).

84. A method for preparing a composition according to claim 70, wherein the method comprises
- injection molding of a melted or semi-solid mixture of the matrix composition components into a suitable form,
- application of the coating by injection molding and
- cooling the thus prepared coated composition to solidify the composition.

* * * * *

UNITED STATES PATENT AND TRADEMARK OFFICE
CERTIFICATE OF CORRECTION

PATENT NO. : 8,298,581 B2  
APPLICATION NO. : 10/550685  
DATED : October 30, 2012  
INVENTOR(S) : Gina Fischer et al.

Page 1 of 1

It is certified that error appears in the above-identified patent and that said Letters Patent is hereby corrected as shown below:

On the title page:

Change the assignee, (item 73) from: "EGALET A/S" to: -- EGALET LTD. --.

Signed and Sealed this  
Sixteenth Day of July, 2013

Teresa Stanek Rea  
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,298,581 B2 | Page 1 of 1 |
| APPLICATION NO. | : 10/550685 | |
| DATED | : October 30, 2012 | |
| INVENTOR(S) | : Fischer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1367 days.

Signed and Sealed this
Twenty-sixth Day of August, 2014

Michelle K. Lee
*Deputy Director of the United States Patent and Trademark Office*